(12) United States Patent
Hellerstein et al.

(10) Patent No.: US 9,134,319 B2
(45) Date of Patent: Sep. 15, 2015

(54) METHOD FOR REPLACING BIOMARKERS OF PROTEIN KINETICS FROM TISSUE SAMPLES BY BIOMARKERS OF PROTEIN KINETICS FROM BODY FLUIDS AFTER ISOTOPIC LABELING IN VIVO

(71) Applicants: The Regents of the University of California, Oakland, CA (US); KineMed, Inc., Emeryville, CA (US)

(72) Inventors: Marc K. Hellerstein, Kensington, CA (US); Martin Decaris, Oakland, CA (US); Mahalakshmi Shankaran, Fremont, CA (US)

(73) Assignees: The Regents of the University of California, Oakland, CA (US); KineMed, Inc., Emeryville, CA (US)

( * ) Notice: Subject to any disclaimer, the term of this patent is extended or adjusted under 35 U.S.C. 154(b) by 0 days.

(21) Appl. No.: 14/210,415

(22) Filed: Mar. 13, 2014

(65) Prior Publication Data
US 2014/0273044 A1   Sep. 18, 2014

Related U.S. Application Data

(60) Provisional application No. 61/801,815, filed on Mar. 15, 2013.

(51) Int. Cl.
*C12Q 1/48* (2006.01)
*G01N 33/68* (2006.01)

(52) U.S. Cl.
CPC .... *G01N 33/6848* (2013.01); *G01N 2333/9123* (2013.01); *G01N 2800/52* (2013.01)

(58) Field of Classification Search
USPC .................................. 424/9.1, 1.11; 530/350
See application file for complete search history.

(56) References Cited

U.S. PATENT DOCUMENTS

| | | |
|---|---|---|
| 4,065,552 A | 12/1977 | Costa |
| 4,332,784 A | 6/1982 | Smith et al. |
| 4,889,126 A | 12/1989 | Doddrell et al. |
| 4,940,658 A | 7/1990 | Allen et al. |
| 5,026,909 A | 6/1991 | Zolotarev et al. |
| 5,042,488 A | 8/1991 | Ackerman |
| 5,167,948 A | 12/1992 | Wenzel |
| 5,209,919 A | 5/1993 | Turteltaub et al. |
| 5,317,098 A | 5/1994 | Shizuya et al. |
| 5,338,686 A | 8/1994 | Hellerstein |
| 5,354,662 A | 10/1994 | Stone et al. |
| 5,376,355 A | 12/1994 | Turteltaub et al. |
| 5,394,236 A | 2/1995 | Murnick |
| 5,432,058 A | 7/1995 | Lange, III et al. |
| 5,439,803 A | 8/1995 | Ross et al. |
| 5,506,147 A | 4/1996 | Kolhouse et al. |
| 5,597,548 A | 1/1997 | Sherry et al. |
| 5,665,377 A | 9/1997 | Gonella |
| 5,665,562 A | 9/1997 | Cook |
| 5,783,445 A | 7/1998 | Murnick |
| 5,855,921 A | 1/1999 | Somlyai |
| 5,910,403 A | 6/1999 | Hellerstein |
| 5,916,537 A | 6/1999 | Kajiwara et al. |
| 5,922,554 A | 7/1999 | Fielding et al. |
| 5,924,995 A | 7/1999 | Klein et al. |
| 5,961,470 A | 10/1999 | Wagner et al. |
| 6,010,846 A | 1/2000 | Hellerstein |
| 6,031,228 A | 2/2000 | Abramson |

(Continued)

FOREIGN PATENT DOCUMENTS

| | | |
|---|---|---|
| AU | 2002365268 B2 | 9/2003 |
| CA | 2464474 A1 | 7/2003 |

(Continued)

OTHER PUBLICATIONS

Decaris M. et al. Proteomic Analysis of Altered Extracellular Matrix Turnover in Bleomycin Induced Pulmonary Fibrosis. Molecular & Cellular Proteomics 13(7)1741-1752, Jul. 2014.*
Hellerstein M. New Stable Isotope Mass Spectrometric Techniques for Measuring Fluxes Through Intact Metaboic Pathways in Mammalian Systems. Metabolic Engineering 6(1)85-100, Jan. 2004.*
Price J. et al. The Effect of Long Term Calorie Restriction on In Vivo Hepatic Proteostatis. Molecular & Cellular Proteomics 11(12)1801-1814 Dec. 2012.*
Extended European Search Report (includes Supplementary European Search Report and Search Opinion) received for European Patent Application No. 12830717.0, mailed on Jan. 30, 2015, 8 pages.
Turner et al., "Dissociation between Adipose Tissue Fluxes and Lipogenic Gene Expression in ob/ob Mice", Am. J. Physiol. Endocrinol. Metab., vol. 292, 2006, pp. E1101-E1109.

(Continued)

*Primary Examiner* — Ralph Gitomer
(74) *Attorney, Agent, or Firm* — Morrison & Foerster LLP

(57) ABSTRACT

Provided herein are method for measuring the rate of synthesis, breakdown, transport, or other kinetic parameters of a protein in a tissue of medical interest, without requiring physical sampling of the tissue, by a measurement of the protein in a body fluid. Methods may include selecting one or more target proteins in a tissue; administering an isotope-labeled molecule to a subject for a period of time sufficient for said isotope-labeled molecule to enter into and label the one or more target proteins to produce one or more isotope-labeled target proteins; collecting a volume of a body fluid, wherein the volume comprises one or more isotope-labeled target proteins that escaped or were released from the tissue; enriching or isolating the one or more isotope-labeled target proteins from the volume; performing a mass spectrometric measurement of the isotopic content, rate of incorporation, and/or pattern or rate of change in isotopic content and/or pattern of isotope labeling of the one or more enriched or isolated isotope-labeled target proteins; and calculating at least one kinetic parameter of the one or more enriched or isolated isotope-labeled target proteins, where the kinetic parameter of the one or more isotope-labeled target proteins from the volume of a body fluid reflects the corresponding kinetic parameter of the one or more target proteins in the tissue; and inferring the at least one kinetic parameter of the one or more target proteins in the tissue based on the corresponding at least one kinetic parameter of the one or more target proteins in the body fluid.

26 Claims, 12 Drawing Sheets

(56) References Cited

U.S. PATENT DOCUMENTS

| | | | |
|---|---|---|---|
| 6,071,245 A | 6/2000 | Kohno et al. |
| 6,117,656 A | 9/2000 | Seed |
| 6,284,219 B1 | 9/2001 | Ajami |
| 6,306,660 B1 | 10/2001 | Messenger et al. |
| 6,329,208 B1 | 12/2001 | Jones et al. |
| 6,355,416 B1 | 3/2002 | Abramson |
| 6,461,806 B1 | 10/2002 | Hellerstein |
| 6,461,870 B2 | 10/2002 | Yatscoff et al. |
| 6,468,802 B1 | 10/2002 | Yatscoff et al. |
| 6,566,086 B1 | 5/2003 | Al Athel et al. |
| 6,599,750 B2 | 7/2003 | Yatscoff et al. |
| 6,602,715 B2 | 8/2003 | Yatscoff et al. |
| 6,610,270 B1 | 8/2003 | Ajami |
| 6,625,547 B1 | 9/2003 | Korzekwa et al. |
| 6,642,059 B2 | 11/2003 | Chait et al. |
| 6,653,076 B1 | 11/2003 | Franza, Jr. et al. |
| 6,653,090 B1 | 11/2003 | Lopaschuk |
| 6,670,194 B1 | 12/2003 | Aebersold et al. |
| 6,680,203 B2 | 1/2004 | Dasseux et al. |
| 6,764,817 B1 | 7/2004 | Schneider |
| 6,783,751 B2 | 8/2004 | Heumann |
| 6,808,875 B2 | 10/2004 | Hellerstein |
| 6,835,927 B2 | 12/2004 | Becker et al. |
| 6,849,396 B2 | 2/2005 | Schneider |
| 6,872,575 B2 | 3/2005 | Regnier |
| 6,887,712 B1 | 5/2005 | Medford et al. |
| 6,902,719 B2 | 6/2005 | Wagner |
| 6,906,320 B2 | 6/2005 | Sachs et al. |
| 7,001,587 B2 * | 2/2006 | Hellerstein | 424/9.1 |
| 7,022,834 B2 | 4/2006 | Hellerstein |
| 7,048,907 B2 | 5/2006 | Groman et al. |
| 7,057,168 B2 | 6/2006 | Miller et al. |
| 7,084,396 B2 | 8/2006 | Schneider |
| 7,255,850 B2 | 8/2007 | Hellerstein |
| 7,256,047 B2 | 8/2007 | Malloy et al. |
| 7,262,020 B2 | 8/2007 | Hellerstein |
| 7,307,059 B2 * | 12/2007 | Hellerstein | 424/1.49 |
| 7,357,913 B2 | 4/2008 | Hellerstein |
| 7,410,633 B2 | 8/2008 | Hellerstein |
| 7,449,171 B2 | 11/2008 | Hellerstein |
| 7,504,233 B2 | 3/2009 | Hellerstein |
| 7,873,198 B2 | 1/2011 | Shepherd et al. |
| 7,910,323 B2 | 3/2011 | Hellerstein |
| 8,005,623 B2 * | 8/2011 | Hellerstein | 702/19 |
| 8,021,644 B2 | 9/2011 | Hellerstein |
| 8,084,016 B2 * | 12/2011 | Hellerstein | 424/9.1 |
| 8,129,335 B2 * | 3/2012 | Hellerstein | 514/1.1 |
| 8,401,800 B2 * | 3/2013 | Hellerstein | 702/19 |
| 8,481,478 B2 | 7/2013 | Hellerstein |
| 8,574,543 B2 * | 11/2013 | Lee et al. | 424/1.69 |
| 8,849,581 B2 | 9/2014 | Hellerstein |
| 2003/0068634 A1 | 4/2003 | Hellerstein |
| 2003/0119069 A1 | 6/2003 | Schneider et al. |
| 2003/0133871 A1 | 7/2003 | Hellerstein |
| 2003/0148533 A1 | 8/2003 | Malloy et al. |
| 2003/0180710 A1 | 9/2003 | Lee et al. |
| 2003/0180800 A1 | 9/2003 | Lee et al. |
| 2003/0211036 A1 | 11/2003 | Degani et al. |
| 2003/0224420 A1 | 12/2003 | Hellerstein et al. |
| 2003/0228259 A1 | 12/2003 | Hellerstein |
| 2004/0081994 A1 | 4/2004 | Hellerstein |
| 2004/0091943 A1 | 5/2004 | Schneider |
| 2004/0115131 A1 | 6/2004 | Hellerstein |
| 2004/0121305 A1 | 6/2004 | Wiegand et al. |
| 2004/0152994 A1 | 8/2004 | Meier-Augenstein |
| 2004/0191916 A1 | 9/2004 | Gross et al. |
| 2004/0253647 A1 | 12/2004 | Mathews et al. |
| 2005/0003375 A1 | 1/2005 | Franza, Jr. et al. |
| 2005/0014181 A1 | 1/2005 | Galis et al. |
| 2005/0019251 A1 | 1/2005 | Hellerstein |
| 2005/0092910 A1 | 5/2005 | Geromanos et al. |
| 2005/0118724 A1 | 6/2005 | Bateman et al. |
| 2005/0147558 A1 | 7/2005 | Hellerstein |
| 2005/0153346 A1 | 7/2005 | Schneider |
| 2005/0175982 A1 | 8/2005 | Iwatani et al. |
| 2005/0180949 A1 | 8/2005 | Emtage et al. |
| 2005/0201937 A1 | 9/2005 | Hellerstein |
| 2005/0202406 A1 | 9/2005 | Hellerstein |
| 2005/0221278 A1 | 10/2005 | Iwatani et al. |
| 2005/0238577 A1 | 10/2005 | Hellerstein |
| 2005/0238581 A1 | 10/2005 | Kurland et al. |
| 2005/0255509 A1 | 11/2005 | Hellerstein et al. |
| 2005/0281745 A1 | 12/2005 | Lee et al. |
| 2006/0008796 A1 | 1/2006 | Hellerstein |
| 2006/0029549 A1 | 2/2006 | Hellerstein |
| 2006/0094057 A1 | 5/2006 | Hellerstein |
| 2006/0100903 A1 | 5/2006 | Lee et al. |
| 2006/0105322 A1 | 5/2006 | Iwatani et al. |
| 2006/0105339 A1 | 5/2006 | Hellerstein |
| 2006/0120961 A1 | 6/2006 | Schneider et al. |
| 2006/0204439 A1 | 9/2006 | Hellerstein |
| 2006/0251576 A1 | 11/2006 | Hellerstein |
| 2006/0280682 A1 | 12/2006 | Hellerstein |
| 2006/0281188 A1 | 12/2006 | Mann et al. |
| 2007/0248540 A1 | 10/2007 | Hellerstein |
| 2008/0003179 A1 | 1/2008 | Hellerstein |
| 2008/0128608 A1 | 6/2008 | Northen et al. |
| 2009/0041661 A1 | 2/2009 | Hellerstein |
| 2009/0042741 A1 | 2/2009 | Northen et al. |
| 2009/0087913 A1 | 4/2009 | Sakuma |
| 2010/0056392 A1 | 3/2010 | Greving et al. |
| 2010/0099891 A1 | 4/2010 | Okuno et al. |
| 2010/0317541 A1 | 12/2010 | Addington et al. |
| 2011/0195865 A1 | 8/2011 | Hellerstein |
| 2014/0005074 A1 | 1/2014 | Hellerstein |
| 2014/0162900 A1 | 6/2014 | Hellerstein |
| 2014/0186838 A1 | 7/2014 | Hellerstein |
| 2014/0193828 A1 | 7/2014 | Hellerstein |
| 2014/0287957 A1 * | 9/2014 | Prusiner et al. | 506/12 |
| 2014/0295484 A1 | 10/2014 | Hellerstein |
| 2014/0295485 A1 | 10/2014 | Hellerstein |
| 2014/0329274 A1 | 11/2014 | Bowen et al. |
| 2014/0353486 A1 | 12/2014 | Leonard |

FOREIGN PATENT DOCUMENTS

| | | |
|---|---|---|
| CA | 2494715 A1 | 2/2004 |
| CA | 2530789 A1 | 4/2005 |
| CA | 2840691 A1 | 4/2005 |
| CA | 2858368 A1 | 6/2013 |
| EP | 0826377 B1 | 11/2002 |
| EP | 1437966 A1 | 7/2004 |
| EP | 1663319 A2 | 6/2006 |
| EP | 2753707 A1 | 7/2014 |
| EP | 2788772 A1 | 10/2014 |
| JP | 2001-211782 A | 8/2001 |
| JP | 2003-502016 A | 1/2003 |
| JP | 2003-79270 A | 3/2003 |
| JP | 2014-526685 A | 10/2014 |
| SU | 968036 A1 | 10/1982 |
| WO | 90/11371 A1 | 10/1990 |
| WO | 93/20800 A1 | 10/1993 |
| WO | 93/25705 A1 | 12/1993 |
| WO | 95/13096 A1 | 5/1995 |
| WO | 98/51820 A1 | 11/1998 |
| WO | 00/12535 A2 | 3/2000 |
| WO | 00/13025 A1 | 3/2000 |
| WO | 00/55355 A2 | 9/2000 |
| WO | 00/63683 A1 | 10/2000 |
| WO | 01/80715 A2 | 11/2001 |
| WO | 01/84143 A1 | 11/2001 |
| WO | 03/061479 A1 | 7/2003 |
| WO | 03/068919 A2 | 8/2003 |
| WO | 03/087314 A2 | 10/2003 |
| WO | 2004/003493 A2 | 1/2004 |
| WO | 2004/011426 A2 | 2/2004 |
| WO | 2004/016156 A2 | 2/2004 |
| WO | 2004/021863 A2 | 3/2004 |
| WO | 2004/024941 A2 | 3/2004 |
| WO | 2004/025270 A2 | 3/2004 |
| WO | 2004/042360 A2 | 5/2004 |
| WO | 2004/016156 A3 | 6/2004 |
| WO | 2005/009597 A2 | 2/2005 |
| WO | 2005/015155 A2 | 2/2005 |

(56) References Cited

FOREIGN PATENT DOCUMENTS

| WO | 2005/033652 A2 | 4/2005 |
|---|---|---|
| WO | 2005/051434 A1 | 6/2005 |
| WO | 2005/087943 A1 | 9/2005 |
| WO | 2006/050130 A2 | 5/2006 |
| WO | 2006/081521 A2 | 8/2006 |
| WO | 2006/107814 A2 | 10/2006 |
| WO | 2010/136455 A1 | 12/2010 |
| WO | 2011/004009 A1 | 1/2011 |
| WO | 2013/036885 A1 | 3/2013 |
| WO | 2013/086070 A1 | 6/2013 |
| WO | 2014/201291 A1 | 12/2014 |

OTHER PUBLICATIONS

Written Opinion mailed Jul. 14, 2006, by the Australian Patent Office for Singapore patent application No. 200502593-7, filed on Nov. 4, 2003, 5 pages.
Australian Search Report and Written Opinion mailed Aug. 5, 2009, for SG Application No. 200717391-7, filed on May 3, 2006, 7 pages.
Supplementary Partial Search Report Received for European Patent Application No. 02806603.3, mailed on Jul. 25, 2006, 5 pages.
Supplementary Partial Search Report received for European Patent Application No. 03713429.3, mailed on Mar. 22, 2006, 6 pages.
Supplementary Partial Search Report received for European Patent Application No. 03749756.7, mailed on Aug. 17, 2005, 6 pages.
Supplementary Partial Search Report received for European Patent Application No. 03768624.3, mailed on Sep. 22, 2006, 4 pages.
Supplementary Search Report received for European Patent Application No. 04809469.2, mailed on Jul. 28, 2009, 4 pages.
Search Report received for European Patent Application No. 04812281.6, mailed on Oct. 6, 2010, 4 pages.
Supplementary Search Report received for European Patent Application No. 05725448.4, mailed on Jun. 30, 2009, 7 pages.
International Search Report received for PCT Patent Application No. PCT/US1998/009479, mailed on Oct. 20, 1998, 3 pages.
Supplementary Search Report received for European Patent Application No. 05733311.4, mailed on Sep. 19, 2008, 9 pages.
International Search Report received for for PCT Patent Application No. PCT/US2003/004183, mailed on Jun. 29, 2004, 4 pages.
International Search Report received for for PCT Patent Application No. PCT/US2003/010554, mailed on Aug. 20, 2004, 4 pages.
International Search Report received for PCT Patent Application No. PCT/US2003/020052, mailed on Apr. 13, 2004, 3 pages.
International Search Report received for PCT Patent Application No. PCT/US2003/023340, mailed on Aug. 18, 2004, 4 pages.
International Search Report received for PCT Patent Application No. PCT/US2003/027623, mailed on Jul. 8, 2004, 4 pages.
International Search Report received for PCT Patent Application No. PCT/US2003/029361, mailed on Jan. 19, 2005, 4 pages.
International Search Report received for PCT Patent Application No. PCT/US2003/29526, mailed on Aug. 18, 2004, 3 pages.
International Search Report received for PCT Patent Application No. PCT/US2003/035107, mailed on Jul. 9, 2004, 2 pages.
International Search Report received for PCT Patent Application No. PCT/US2004/21063, mailed on Apr. 4, 2005, 2 pages.
International Search Report received for PCT Patent Application No. PCT/US2004/039722, mailed on Mar. 25, 2005, 3 pages.
International Search Report and Written Opinion received for PCT Patent Application No. PCT/US2005/005660, mailed on Oct. 11, 2007, 11 pages.
International Search Report and Written Opinion received for PCT Patent Application No. PCT/US2005/010429, mailed on Aug. 8, 2006, 15 pages.
International Search Report received for PCT Patent Application No. PCT/US2005/08265, mailed on Aug. 1, 2005.4 pages.
International Search Report and Written Opinion received for PCT Patent Application No. PCT/US2006/017167, mailed on Feb. 5, 2008, 11 pages.
"NCBI Blast: Protein Sequence (17 letters)", Available at <http://blast.ncbi.nlm.nih.gov/Blast.cgi>, Visited on May 29, 2008, 5 pages.
"New Diagnostic Technique Could Help Treat AIDS", Agence France-Presse, Dow Jones News, Feb. 17, 1998, pp. 1-2.
Zilversmit et al., "On the Calculation of 'Turnover Time' and 'Turnover Rate' from Experiments Involving the Use of Labeling Agents", J. of General Physiology, vol. 26, No. 3, 1943, pp. 325-331.
Ackermans et al., "The Quantification of Gluconeogenesis in Healthy Men by 2H2O and [2-13C]Glycerol Yields Different Results: Rates of Gluconeogenesis in Helathy Men Measured with 2H2O are Higher than those Measured with [2-13C]Glycerol", The Journal of Clinical Endocrinology & Metabolism, vol. 86, No. 5, 2001, pp. 2220-2226.
Adami et al., "The Aetiology and Pathogenesis of Human Breast Cancer", Mutation Research, vol. 333, 1995, pp. 29-35.
Airhart et al., "Compartmentation of Free Amino Acids for Protein Synthesis in Rat Liver", The Biochemical Journal, vol. 140, 1974, pp. 539-545.
Ajie et al., "In Vivo Study of the Biosynthesis of Long-Chain Fatty Acids Using Deuterated Water", The American Journal of Physiology, vol. 269, 1995, pp. E247-E252.
Anderson et al., "Direct HIV Cytopathicity Cannot Account for CD4 Decline in AIDS in the Presence of Homeostasis: A Worst-Case Dynamic Analysis", Journal of Acquired Immune Deficiency Syndromes and Human Retrovirology, vol. 17, 1998, pp. 245-252.
Antelo et al., "Adipose Triglyceride (TG) Turnover and De Novo Lipogenesis (DNL) in Humans: Measurement by Long-Term 2H2O Labeling and Mass Isotopomer Distribution Analysis (MIDA)", Experimental Biology, FASEB#361.10, 2002, p. A400 (Abstract only).
Asher et al., "Evaluation of Cell Death in EBV-Transformed Lymphocytes Using Agarose Gel Electrophoresis, Light Microscopy and Electron Microscopy. II. Induction of Non-Classic Apoptosis ("Para-Apoptosis") by Tritiated Thymidine", Leukemia & Lymphoma, vol. 19, 1995, pp. 107-119.
Attardi et al., "Biogenesis of Mitochondria", Annual Review of Cell Biology, vol. 4, 1988, pp. 289-333.
Bach et al., "Stem Cells: The Intestinal Stem Cell as a Paradigm", Carcinogenesis, vol. 21, No. 3, 2000, pp. 469-476.
Backhouse et al., "Effects of Haloperiodol on Cell Proliferation in the Early Postnatal Rat Brain", Neuropathology and Applied Neurobiology, vol. 8, No. 2, 1982, pp. 109-116.
Bandsma et al., "Contribution of Newly Synthesized Cholesterol to Rat Plasma and Bile Determined by Mass Isotopomer Distribution Analysis: Bile-Salt Flux Promotes Secretion of Newly Synthesized Cholesterol into Bile", The Biochemical Journal, vol. 329, 1998, pp. 699-703.
Bandsma et al., "The Contribution of Newly Synthesized Cholesterol to Bile Salt Synthesis in Rats Quantified by Mass Isotopomer Distribution Analysis", Biochimica et Biophysica Acta, vol. 1483, 2000, pp. 343-351.
Bertani et al., "Measurement of Total Body Water (TBW) Through In Vivo Dilution of Tracer Compounds: Use of D2O and its Determination by FT Infrared Spectroscopy", Annali Di Chimica, vol. 92, 2002, pp. 135-138.
Bickenbach, "Identification and Behavior of Label-Retaining Cells in Oral Mucosa and Skin", Journal of Dental Research, vol. 60, 1981, pp. 1611-1620.
Bier, D. M., "The Use of Stable Isotopes in Metabolic Investigation", Balliere's Clinical Endocrinology and Metabolism, vol. 1, No. 4, Nov. 1987, pp. 817-836.
Bier, D. M., "Stable Isotopes in Biosciences, their Measurement and Models for Amino Acid Metabolism", European Journal of Pediatrics, vol. 156, 1997, pp. S2-S8.
Bingham, Sheila A., "The Use of 24-h Urine Samples and Energy Expenditure to Validate Dietary Assessments", The American Journal of Clinical Nutrition, vol. 59(suppl), 1994, pp. 227S-231S.
Black et al., "Labeling DNA with Stable Isotopes: Economical and Practical Considerations", BioTechniques, vol. 30, 2001, pp. 134-138, 140.
Blair et al., "Changes in Physical Fitness and All-Cause Mortality. A Prospective Study of Healthy and Unhealthy Men", JAMA, vol. 273, 1995, pp. 1093-1098.
Blau et al., "Handbook of Derivatives for Chromatography", 2nd Edition, John Wiley & Sons Ltd., England, 1993.

(56) References Cited

OTHER PUBLICATIONS

Bonotto et al., "Study of the Distribution and Biological Effects of 3H in the Algae Acetabularia, Chlamydomonas and Porphyra", Current Topics in Radiation Research Quarterly, vol. 12, 1978, pp. 115-132.
Boros et al., "Genistein Inhibits Nonoxidative Ribose Synthesis in MIA Pancreatic Adenocarcinoma Cells: A New Mechanism of Controlling Tumor Growth", Pancreas, vol. 22, No. 1, 2001, pp. 1-7.
Jiang et al., Rb Deletion in Mouse Mammary Progenitors Induces Luminal-B or Basal-like/EMT Tumor Subtypes Depending on p53 Status, The Journal of Clinical Investigation, vol. 120, No. 9, Sep. 2010, pp. 3296-3309.
Jones et al., "Multiple Statistical Analysis Techniques Corroborate Intratumor Heterogeneity in Imaging Mass Spectrometry Datasets of Myxofibrosarcoma", Plos One, Sep. 29, 2011, 11 pages.
Jurchen et al., "MALDI-MS Imaging of Features Smaller than the Size of the Laser Beam", Journal of American Society for Mass Spectrometry, vol. 16, Aug. 10, 2005, pp. 1654-1659.
Kasumov et al., "Measuring Protein Synthesis using Metabolic 2H Labeling, High-Resolution Mass Spectrometry, and an Algorithm", Analytical Biochemistry, vol. 412, 2011, pp. 1-9.
Kennecke et al., "Metastatic Behavior of Breast Cancer Subtypes", Journal of Clinical Oncology, vol. 28, No. 20, Jul. 2010, pp. 3271-3277.
Koeniger et al., "A Quantitation Method for Mass Spectrometry Imaging", Rapid Communications in Mass Spectrometry, vol. 25, No. 4, 2011, pp. 503-510.
Lechene et al., "High-Resolution Quantitative Imaging of Mammalian and Bacterial Cells using Stable Isotope Mass Spectrometry", Journal of Biology, vol. 5, Article 20, Oct. 2006, pp. 20.1-20.30.
Lee et al., "In Vivo Measurement of Fatty Acids and Cholesterol Synthesis using D20 and Mass Isotopomer Analysis", American Journal of Physiology-Endocrinology and Metabolism, vol. 266, No. 5, 1994, pp. E699-E708.
Lee et al., "Mass Spectrometry-Based metabolomics, Analysis of Metabolite-protein Interactions, and Imaging", BioTechniques, vol. 49, No. 2, Aug. 2010, pp. 557-565.
Lee et al., "Resolving Brain Regions Using Nanostructure Iiitiator Mass Spectrometry Imaging", Integrative Biology, vol. 4, No. 6, Jun. 2012, pp. 693-699.
Liedtke et al., 'Response to Neoadjuvant Therapy and Long-Term Survival in Patients With Triple-Negative Breast Cancer, Journal of Clinical Oncology, vol. 26, No. 8, Mar. 2008, pp. 1275-1281.
Lindwal et al., "Heavy Water Labeling of Keratin as a Non-Invasive Biomarker of Skin Turnover in Vivo in Rodents and Humans", Journal of Investigative Dermatology, vol. 126, 2006, pp. 841-848.
Liu et al., "Polarity and Proliferation are Controlled by Distinct Signaling Pathways Downstream of PI3-kinase in Breast Epithelial Tumor Cells", The Journal of Cell Biology, vol. 164, No. 4, Feb. 16, 2004, pp. 603-612.
Maheo et al., "Differential Sensitization of Cancer Cells to Doxorubicin by DHA: A Role for Lipoperoxidation", Free Radical Biology & Medicine, vol. 39, Issue. 6, Sep. 15, 2005, pp. 742-751.
Marusyk et al., "Tumor Heterogeneity: Causes and Consequences", Biochimical Biophysical Acta, vol. 1805, No. 1, Jan. 2010, pp. 105-117.
McCubrey et al., "Roles of the Raf/MEK/ERK Pathway in Cell Growth, Malignant Transformation and Drug Resistance", Biochimical Biophysical Acta, vol. 1773, 2007, pp. 1263-1284.
McMahon et al., "Quantitative Imaging of Cells with Multiisotope Imaging Mass Spectrometry (MIMS)-Nanoautography with Stable Isotope Tracers", National Resource for Imaging Mass Spectrometry, vol. 252, Issue 19, Jul. 30, 2006, pp. 6895-6906.
Murphy et al., "Imaging of Lipid Species by MALDI Mass Spectrometry", Journal of Lipid Research, Apr. 2009, pp. S317-S322.
Neve et al., "A Collection of Breast Cancer Cell Lines for the Study of Functionally Distinct Cancer Subtypes", Cancer Cell, vol. 10, No. 6, Dec. 2006, pp. 515-527.
Nordstrom et al., "Metabolomics: Moving to the Clinic", Journal of Neuroimmune Pharmacology, vol. 5, No. 1, 2009, pp. 4-17.

Northen et al., "A Nanostructure-Initiator Mass Spectrometry-Based Enzyme Activity Assay", PNAS, vol. 105, No. 10, Mar. 11, 2008, pp. 3678-3683.
Northen et al., "Clathrate Nanostructures for Mass Spectrometry", Nature, vol. 449, Oct. 25, 2007, pp. 1033-1036.
Ogretmen et al., "Biologically Active Sphingolipids in Cancer Pathogenesis and Treatment", Nature Reviews Cancer, vol. 4, No. 8, 2004, pp. 604-616.
International Written Opinion received for PCT Patent Application No. PCT/US2004/039722, mailed on Mar. 25, 2005, 3 pages.
Price et al., "Analysis of Proteome Dynamics in the Mouse Brain", PNAS, vol. 107, No. 32, Aug. 10, 2010, pp. 14508-14513.
Quehenberger et al., "The Human Plasma Lipidome", The New England Journal of Medicine, vol. 365, No. 19, Nov. 2011, pp. 1812-1823.
Reindl et al., "Multivariate Analysis of a 3D Mass Spectral Image for Examining Tissue Heterogeneity", Integrative Biology, vol. 3, No. 4, Apr. 2011, pp. 460-467.
Reindl et al., "Rapid Screening of Fatty Acids Using Nanostructurelnitiator Mass Spectrometry", Analytical Chemistry, vol. 82, No. 9, 2010, pp. 3751-3755.
Reis-Filho et al., "Triple Negative Tumours: A Critical Review", Histopathology, vol. 52, 2008, pp. 108-118.
Robinson et al., "Long-Term Synthesis Rates of Skeletal Muscle DNA and Protein are Higher during Aerobic Training in Older Humans than in Sedentary Young Subjects but are Not Altered by Protein Supplementation", The FASEB Journal, vol. 25 No. 9, 2011, pp. 3240-3249.
Rockwood et al., "Dissociation of Individual Isotopic Peaks: Predicting Isotopic Distributions of Product Ions in MSn", American Society for Mass Spectrometry, Jan. 18, 2003, pp. 311-322.
Rockwood et al., "Rapid Calculation of Isotope Distributions", Analytical Chemistry, vol. 67, No. 15, 1995, pp. 2699-2704.
Rockwood et al., "Ultrahigh-Speed Calculation of Isotope Distributions", Analytical Chemistry, vol. 68, No. 13, 1996, pp. 2027-2030.
Roddy et al., "Imaging of Freeze-Fractured Cells with in Situ Fluorescence and Time-of-Flight Secondary Ion Mass Spectrometry", Analytical Chemistry, vol. 74, No. 16, 2002, pp. 4011-4019.
Schiller et al., "Matrix-Assisted Laser Desorption and Ionization Time-of-Flight (MALDI-TOF) Mass Spectrometry in Lipid and Phospholipid Research", Progress in Lipid Research, vol. 43, 2004, pp. 449-488.
Schwamborn et al., "R.M. Molecular Imaging by Mass Spectrometry-Looking Beyond Classical Histology", Nature Reviews Cancer, vol. 10, 2010, pp. 639-646.
Spector et al., "Membrane Lipid Composition and Cellular Function", Journal of Lipid Research, vol. 26, 1985, pp. 1015-1035.
Sperling et al., "Quantitative Analysis of Isotope Distributions in Proteomic Mass Spectrometry Using Least-Squares Fourier Transform Convolution", Analytical Chemistry, vol. 80, No. 13, Jul. 1, 2008, pp. 4906-4917.
Swinnen et al., "Increased Lipogenesis in Cancer Cells: New Players, Novel Targets", Current Opinion in Clinical Nutrition and Metabolic Care, vol. 9, 2006, pp. 358-365.
Takats et al., "Mass Spectrometry Sampling Under Ambient Conditions with Desorption Electrospray Ionization", Science, vol. 306, Oct. 2004, pp. 471-473.
Tennant et al., "Metabolic Transformation in Cancer", Carcinogenesis, vol. 30, No. 8, 2009, pp. 1269-1280.
Trere et al., "High Prevalence of Retinoblastoma Protein Loss in Triple-Negative Breast Cancers and its Association with a Good Prognosis in Patients Treated with Adjuvant Chemotherapy", Annals of Oncology, vol. 20, No. 11, Nov. 2009, pp. 1818-1823.
Viale et al., "Current Concepts on Hyperpolarized Molecules in MRI", Current Opinion in Chemical Biology, vol. 14, No. 1, 2010, pp. 90-96.
Weigelt et al., "Breast Cancer Metastasis: Markers and Models", Nature, vol. 5, Aug. 2005, pp. 591-602.
Winograd et al., "Improvements in SIMS Continueis the End in Sight?", Applied Surface Science, vol. 252, No. 19, 2006, pp. 6836-6843.

(56) References Cited

OTHER PUBLICATIONS

Wiseman et al., "Desorption Electrospray Ionization Mass Spectrometry: Imaging Drugs and Metabolites in Tissues", Proceedings of the National Academy of Sciences, vol. 105, No. 47, Nov. 25, 2008, pp. 18120-18125.
Yanes et al., Nanostructure Initiator Mass Spectrometry: Tissue Imaging and Direct Biofluid Analysis, Anal Chem., vol. 81, No. 8, Apr. 2009, pp. 2969-2975.
Yecies et al., "Transcriptional Control of Cellular Metabolism by mTOR Signaling", Cancer Research, vol. 71, No. 8, Apr. 15, 2011, pp. 2815-2820.
Yoshimura et al., "Real-Time Analysis of Living Animals by Electrospray Ionization Mass Spectrometry", Anal Biochemistry, vol. 417, No. 2, Oct. 2011, pp. 195-201.
Zeisel, S. H.. "Choline: An Essential Nutrient for Humans", Nutrition, vol. 16, 2000, pp. 669-671.
Rittenberg et al., "Deuterium as an Indicator in the Study of Intermediary Metabolism—VIII. Hydrogenation of Fatty Acids in the Animal Organism", Journal of Biological Chemistry, vol. 117, Feb. 1937, pp. 485-490.
Rittenberg et al., "Deuterium as an Indicator in the Study of Intermediary Metabolism—X. The Metabolism of Butyric and Caproic Acids", Journal of Biological Chemistry, vol. 120, Sep. 1937, pp. 503-510.
Rittler et al., "Effect of Tumor Removal on Mucosal Protein Synthesis in Patients with Colorectal Cancer", American Journal of Physiology-Endocrinology and Metabolism, vol. 284, 2003, pp. E1018-E1021.
Roberts, S. B., "Use of the Doubly Labeled Water Method for Measurement of Energy Expenditure, Total Body Water, Water Intake, and Metabolizable Energy Intake in Humans and Small Animals", Can. J. Physiol. Pharmacol., vol. 67, No. 10, 1989, pp. 1190-1198.
Robin et al., "Mitochondria DNA Molecules and Virtual Number of Mitochondria per Cell in Mammalian Cells", Journal of Cellular Physiology, vol. 136, 1988, pp. 507-513.
Robosky, L. C., "In Vivo Toxicity Screening Programs Using Metabonomics", Combinatorial Chemistry & High Throughput Screening., vol. 5, 2002, pp. 651-662.
Rocha et al., "Accumulation of Bromodeoxyuridine-Labelled Cells in Central and Peripheral Lymphoid Organs: Minimal Estimates of Production and Turnover Rates of Mature Lymphocytes", Eur. J. Immunol., vol. 20, 1990, pp. 1697-1708.
Roda et al., "Results with Six 'Kit' Radioimmunoassays for Primary Bile Acids in Human Serum Intercompared", Clin. Chem., vol. 26, No. 12, 1980, pp. 1677-1682.
Roederer, M., "T-Cell Dynamics of Immunodeficiency", Nature Medicine, vol. 1, No. 7, Jul. 1995, pp. 621-622.
Rooyackers et al., "Tracer Kinetics Are of Limited Value to Measure In Vivo Protein Synthesis and Degradation Rates in Muscle of Anesthetized Rats", Metabolism, vol. 45, No. 10, Oct. 1996, pp. 1279-1283.
Rosin et al., "The Use of Exfoliative Cell Samples to Map Clonal Genetic Alterations in the Oral Epithelium of High-Risk Patients", Cancer Research, vol. 57, Dec. 1, 1997, pp. 5258-5260.
Royale et al., "Techniques for Investigating Substrate Metabolism in Patients", Annals of the Royal College of Surgeons of England, vol. 63, 1981, pp. 415-419.
Santarelli et al., "Requirement of Hippocampal Neurogenesis for the Behavioral Effects of Antidepressants", Science, vol. 301, No. 5634, Aug. 8, 2003, pp. 805-809.
Sawada et al., "Comparison of Autoradiography, Liquid Scintillation Counting and Immunoenzymatic Staining of 5-bromo-2'-deoxyuridine for Measurement of Unscheduled DNA Synthesis and Replicative DNA Synthesis in Rat Liver", Mutation Research, vol. 344, 1995, pp. 109-116.
Scalise, K., "Tracking T-Cells in Aids Patients: A Safe Reliable Method of Measuring Human Cell Generation Rates", Berkeleyan, Feb. 11-17, 1998, 3 pages.

Scheibner et al., "Bile Acid Synthesis from Newly Synthesized Vs. Preformed Cholesterol Precursor Pools in the Rat", Hepatology, vol. 17, 1993, pp. 1095-1102.
Scheibner et al., "Complex Feedback Regulation of Bile Acid Synthesis in the Hamster. The Role of Newly Synthsized Cholesterol", Hepatology, vol. 30, 1999, pp. 230-237.
Schneiter et al., "Kinetics of Dexamethasone Induced Alterations of Glucose Metabolism in Healthy Humans", American Journal of Physiology, 1998, pp. E806-E813.
Schoenheimer et al., "Deuterium as an Indicator in the Study of Intermediary Metabolism—V. The Desaturation of Fatty Acids in Organism", Journal of Biological Chemistry, vol. 113, Mar. 1936, pp. 505-510.
Schwarz et al., "Short-Term Alterations in Carbohydrate Energy Intake in Humans", J. Clin. Invest., vol. 96, 1995, pp. 2735-2743.
Australian Patent Office Search Report mailed Aug. 26, 2005, for Singapore patent application No. SG 200500571-5, filed Jul. 25, 2003, 5 pages.
Shevchenko et al., "Rapid 'de Novo' Peptide Sequencing by a Combination of Nanoelectrospray, Isotopic Labeling and a Quadrupole/Time-of-flight Mass Spectrometer", Rapid Commun. Mass Spectrom., vol. 11, 1997, pp. 1015-1024.
Shigenaga et al., "Assays of Oxidative DNA Damage Biomarkers 8-Oxo-2'-deoxyguanosine and 8-Oxoguanine in Nuclear DNA and Biological Fluids by High-Performance Liquid Chromatography with Electrochemical Detection", Methods in Enzymology, vol. 234, 1994, pp. 16-33.
Siler et al., "De Novo Lipogenesis, Lipid Kinetics, and Whole-Body Lipid Balances in Humans after Acute Alcohol Consumption1-3", American Journal of Clinical Nutrition, vol. 70, 1999, pp. 928-936.
Siler et al., "The Inhibition of Gluconeogenesis Following Alcohol in Humans", Am. J. Physiol., vol. 275, 1998, pp. E897-E907.
Siler et al., "VLDL-Triglyceride Production After Alcohol Ingestion, Studied Using [2-13C1] Glycerol", J. Lipid Res., vol. 39, 1998, pp. 2319-2328.
Smith et al., "The Phosphogluconate Odixative Pathway", in Principles of Biochemistry, 7th edition, McGraw-Hill Book Company, 1983, pp. 417-423.
Sosa-Peinado et al., "Overexpression and Biosynthetic Deuterium Enrichment of TEM-1 Beta-Lactamase for Structural Characterization by Magnetic Resonance Methods", Protein Expression and Purification, vol. 19, No. 2, Jul. 2000, pp. 235-245.
Sprent et al., "CD4+ Cell Turnover", Nature, vol. 375, 1995, 194 pages.
Stingl et al., "Purification and Unique Properties of Mammary Epithelial Stem Cells", Nature, vol. 439, Feb. 2006, pp. 993-997.
Stingl et al., "Characterization of Bipotent Mammary Epithelial Progenitor Cells in Normal Adult Human Breast Tissue", Breast Can Res and Treatment, vol. 67, 2001, pp. 93-109.
Sunter et al., "Cell Population Kinetics in the Epithelium of the Colon of the Male Rat", Virchows Archie. B Cell Path., vol. 26, 1978, pp. 275-287.
Teixeira et al., "Poor CD4 T Cell Restoration After Supression of HIV-1 Replication May Reflect Lower Thymic Function", AIDS, vol. 15, No. 14, 2001, pp. 1749-1756.
Tint et al., "Transformation of 5α-cholest-7-en-3β-ol to Cholesterol and Cholestanol in Cerebrotendinous Xanthomatosis", Journal of Lipid Research, vol. 15, 1974, pp. 256-262.
Traber et al., "Isolation of Intestinal Epithelial Cells for the Study of Differential Gene Expression Along the Crypt-Villus Axis", Am. J. Physiol., vol. 260, 1991, pp. G895-G903.
Trappe et al., "Effect of Ibuprofen and Acetaminophen on Postexercise Muscle Protein Synthesis", Am J Physiology Endocronol Metab, vol. 282, 2002, pp. E551-E556.
Turner, S. M., "Stable Isotopes, Mass Spectrometry, and Molecular Fluxes: Applications to Toxicology", Journal of Pharmacological and Toxicological Methods, vol. 53, 2006, pp. 75-85.
Turner et al., "Emerging Applications of Kinetic Biomarkers in Preclinical and Clinical Drug Development", Current Opinion in Drug Discovery & Development, vol. 8, No. 1, 2005, pp. 115-126.
Turner et al., "Measurement of Triglyceride (TG) Synthesis in Vivo 2H2O Incorporation into TG-Glycerol and Application of Mass

(56) References Cited

OTHER PUBLICATIONS

Isotopomer Distribution Analysis (MIDA)", Experimental Biology, 2002 16 [Meeting Abstract 361.9], A400.

Van Hinsbergh et al., "Palmitate Oxidation by Rat Skeletal Muscle Mitochondria", Archives of Biochemistry and Biophysics, vol. 190, No. 2, 1978, pp. 762-771.

Van Loan et al., "Monitoring Changes in Fat-Free Mass in HIV-Positive Men with Hypotestosteronemia and AIDS Wasting Syndrome Treated with Gonadal Hormone Replacement Therapy", AIDS, vol. 13, 1999, pp. 241-248.

Veenstra et al., "Proteome Analysis Using Selective Incorporation of Isotopically Labeled Amino Acids", J. Am. Soc. Mass. Spectrom., vol. 11, 2000, pp. 78-82.

Veerkamp et al., "14CO2 Production is no. Adequate Measure of [14C]Fatty Acid Oxidation", Biochemical Medicine and Metabolic Biology, vol. 35, 1986, pp. 248-259.

Véniant et al., "Defining the Atherogenicity of Large and Small Lipoproteins Containing Apolipoproteins B100", J. Clin. Invest., vol. 106, No. 12, 2000, pp. 1501-1510.

Wadke et al., "Fatty Acid Synthesis by Liver Perfused with Deuterated and Tritiated Water", Biochemistry, vol. 12, No. 14, 1973, pp. 2619-2624.

Wain-Hobson, S., "Virological Mayhem", Nature, vol. 373, 1995, 102 pages.

Waldeman et al., "A Comparison Between Bromodeoxyuridine and 3 H Thymidine Labeling in Human Breast Tumors", Modern Path., vol. 4, No. 6, 1991, pp. 718-722.

Wang et al., "Effects of Nicotinic Acid on Fatty Acid Kinetics, Fuel Selection, and Pathways of Glucose Production in Women", Am. J. Physiol. Endocrinol. Metab., vol. 279, 2000, pp. E50-E59.

Waterlow, J. C., "Protein Turnover in the Whole Animal", Invest. Cell Pathol. vol. 3, 1980, pp. 107-119.

Wei et al., "Viral Dynamics in Human Immunodeficiency Virus Type 1 Infection", Nature, vol. 373, 1995, pp. 117-122.

Whittmann et al., "Application of MALDI-TOF MS to lysine-Producing Corynebacterium Glutarnicum: A Novel Approach for Metabolic Flux Analysis", Eur. J. Biochem., vol. 268, 2001, pp. 2441-2455.

Winett et al., "Exercise Regimens for Men With HIV", JAMA, vol. 284, No. 2, 2000, pp. 175-176.

Wolf, George, "The Effect of Fasting and Fructose and Glucose Infusion on Gluconeogenesis and Triose Phosphate Flux in Rats in Vivo", Nutrition Reviews, vol. 53, No. 10, 1995, pp. 299-302.

Wolfe, Robert R., "Isotopic Measurement of Glucose and Lactate Kinetics", Ann. Med., vol. 22, 1990, pp. 163-170.

Wolfe et al., "Glucose Metabolism in Humans", ACS Symposium Series 258, Chapter 12, Tumund et al. ed., 1984, pp. 175-189.

Wolthers et al., "Rapid CD4+ T-Cell Turnover in HIV-1 Infection: A Paradigm Revisited", Immunology Today, vol. 19, No. 1, 1998, pp. 44-48.

Wolthers et al, "T Cell Telomere Length in HIV-1 Infection: No Evidence for Increased CD4+ T Cell Turnover", Science, vol. 274, 1996, pp. 1543-1547.

Wong et al., "From monoamines to genomic targets: a paradigm shift for drug discovery in depression", Nature Reviews Drug Discovery, vol. 3, Feb. 2004, pp. 136-151.

Wood et al., "Estimation of Pathways of Carbohydrate Metabolism", Biochemische Zeitschrift, vol. 338, 1963, pp. 809-847.

Zhang et al., "Deuterium NMR Study of the Origin of Hydrogen in Fatty Acids Produced In Vivo in Chicken.", European Journal of Lipid Science and Technology, vol. 108, 2006, pp. 125-133.

Zhang et al., "Kinetics of CD4+ T Cell Repopulation of Lymphoid Tissues after Treatment of HIV-1 Infection", Proc. Natl. Acad. Sci. USA, vol. 95, Feb. 1998, pp. 1154-1159.

Jones et al., "Interaction of Dietary Fat Saturation and Cholesterol Level on Cholesterol Synthesis Measured Using Deuterium Incorporation", Journal of Lipid Research, vol. 35, 1994, pp. 1093-1101.

Pozharisski et al., "Study of Kinetics of Epithelial Cell Populations in Normal Tissues of the Rat's Intestines and in Carcinogenesis", Exp. Path., Bd., vol. 18, 1980, pp. 387-406.

Landau et al., "Use of 2H2O for Estimating Rates of Gluconeogenesis", Journal of Clinical Investigation, vol. 95, Jan. 1995, pp. 172-178.

International Search Report received for PCT Patent Application No. PCT/US2002/033996, mailed on Jun. 19, 2003, 2 pages.

Extended European Search Report received for European Patent Application No. 06784805.1, mailed on Mar. 21, 2011, 7 pages.

Extended European Search Report received for European Patent Application No. 06759050.5, mailed on Mar. 31, 2011, 7 pages.

International Preliminary Report on Patentability received for PCT Patent Application No. PCT/US2004/021063 issued on Jan. 3, 2006, 4 pages.

Abou-Donia et al., "Mechanisms of Joint Neurotoxicity of n-Hexane, Methyl Isobutyl Ketone and O-Ethyl 0-4-Nitrophenyl Phenylphosphonothioate in Hens", The Journal of Pharmacology and Experimental Therapeutics, vol. 257, No. 1, 1991, pp. 282-289.

Abu-Qare et al., "Quantification of Nicotine, Chlorpyrifos and Their Metabolites in Rat Plasma and Urine Using High-Performance Liquid Chromatography", Journal of Chromatography B., vol. 757, 2001, pp. 295-300.

Aydemir et al., "Effects of Defibrotide on Aorta and Brain Malondialdehyde and Antioxidants in Cholesterol-Induced Atherosclerotic Rabbits", International Journal of Clinical 8 Laboratory Research, vol. 30, 2000, pp. 101-107.

Bantscheff et al., "Quantitative Mass Spectrometry in Proteomics: A Critical Review", Anal. Bioanal. Chem., vol. 389, 2007, pp. 1017-1031.

Buchanan, T. A., "Pancreatic Beta-Cell Loss and Preservation in Type 2 Diabetes", Clinical Therapeutics, vol. 25, 2003, pp. B32-B46.

Chobanian et al., "Body cholesterol Metabolism in Man. II. Measurement of the Body Cholesterol Miscible Pool and Turnover Rate", Journal of Clinical Investigation, vol. 41, No. 9, 1962, pp. 1738-1744.

Duane, William C., "Measurement of Bile Acid Synthesis by Three Different Methods in Hypertriglyceridernic and Control Subjects", Journal of Lipid Research, vol. 38, 1997, pp. 183-188.

Edes et al., "Glycemic Index and Insulin Response to a Liquid Nutritional Formula Compared with a Standard Meal", Journal of the American College of Nutrition, vol. 17, No. 1, 1998, pp. 30-35.

Feldman et al., "Chlordiazepoxide-Fluoxetine Interactions on Food Intake in Free-Feeding Rats"', Pharmacology Biochemistry & Behavior, vol. 8, No. 6, 1978, pp. 749-752.

Ferezou et al., "Origins of Neutral Sterols in Human Feces Studied by Stable Isotope Labeling (Deuterium and Carbon-13) Existence of an External Secretion of Cholesterol", Digestion, vol. 21, No. 5, 1981, pp. 232-243.

Futami et al., "An Application of the On-Line Respiratory Mass Spectrometer to the Detection of Helicobacter Pylori Infection Using 13C-Labeled Urea", Journal of the Mass Spectrometry Society of Japan, vol. 47, No. 6, 1999, pp. 386-388.

Jones et al., "Modulation of Plasma Lipid Levels and Cholesterol Kinetics by Phytosterol Versus Phytostanol Esters", Journal of Lipid Research, vol. 41, 2000, pp. 697-705.

Murphy et al., "A New, Sensitive in Vivo Diagnostic Test of Insulin Resistance: The Deuterated Oral Glucose Tolerance Test (2H-OGTT)", Diabetes, American Diabetes Association, US, vol. 53, No. Suppl. 02, Jan. 1, 2004, 2 pages.

Neher et al., "Pyruvate and Thiamine Pyrophosphate Potentiate Cyclic Nucleotide-Induced Steroidogenesis in Isolated Rat Adrenocortical Cells", J.Steroid Biochem., vol. 18, 1983, pp. 1-6

Radziuk, J. "Insulin Sensitivity and its Measurement: Structural Commonalities among the Methods", The Journal of Endocrinology & Metabolism, vol. 85, No. 12, 2000, pp. 4426-4433.

Sakurai, Y. "The Meanings of Measuring Biological Metabolism Using a Stable Isotope Labeled Tracer: The Difference in Metabolism Between a Healthy Human and a Patient in Surgically Serious Condition", Medical Journal of Fukita Academy, vol. 20, No. 1, 1996, pp. 9-21.

Schoenheimer et al., "Deuterium as an Indicator in the Study of Intermediary Metabolism—III. The Role of the Fat Tissues", The Journal of Biological Chemistry, vol. 111, 1935, pp. 175-181.

(56) References Cited

OTHER PUBLICATIONS

Schoenheimer et al., "Deuterium as an Indicator in the Study of Intermediary Metabolism—IX. The Conversion of Stearic Acid into Palmitic Acid in the Organism", The Journal of Biological Chemistry, vol. 120, 1937, pp. 155-165.
Seiler et al., "The Influence of Catabolic Reactions on Polyamine Excretion", Biochem. J., vol. 225, 1985, pp. 219-226.
Shen et al., "Purification of Oligodendrocyte and Its Myelination to the Demyelinated Culture Model in Vitro", Acta Histochem. Cytochem, vol. 35, No. 2, 2002, p. 123.
Tayek et al., "Glucose Production, Recycling, and Gluconeogenesis in Normals and Diabetics: A Mass Isotopomer [U_13C] Glucose Study", Am. J. Physiol. Endocrino.I Metab., vol. 270, No. 4, Apr. 1, 1996, pp. E709-E717.
Wang et al., "Validation of a Single-Isotope-Labeled Cholesterol Tracer Approach for Measuring Human Cholesterol Absorption", Lipids, vol. 39, No. 1, 2004, pp. 87-91.
Written Opinion received for PCT Patent Application No. PCT/US2004/021063 mailed on Apr. 4, 2005, 3 pages.
International Preliminary Report on Patentability received for PCT Patent Application No. PCT/US2004/039722, issued on May 29, 2006, 4 pages.
International Preliminary Report on Patentability received for PCT Patent Application No. PCT/US2005/005660, issued on Oct. 30, 2007, 5 pages.
Comte et al., "Probing the Origin of Acetyl-CoA and Oxaloacetate Entering the Citric Acid Cycle from the 13C Labeling of Citrate Released by Perfused Rat Hearts", The Journal of Biological Chemistry, vol. 272, No. 42, Oct. 17, 1997, pp. 26117-26124.
Hinkson et al., "The Dynamic State of Protein Turnover: It's About Time", Trends in Cell Biology, vol. 21, No. 5, May 2011, pp. 293-303.
Linn et al., "Effect of Long-Term Dietary Protein Intake on Glucose Metabolism in Humans", Diabetologia, vol. 43, 2000, pp. 1257-1265.
Nordhoff et al., "Mass Spectrometry of Nucleic Acids", Mass Spectrometry Reviews, vol. 15, 1996, pp. 67-138.
Previs et al., "A Critical Evaluation of Mass Isotopomer Distribution Analysis of Gluconeogenesis in Vivo", American Journal of Physiology-Endocrinology and Metabolism, vol. 277, 1999, E154-E160.
Price et al., "Measurement of Human Plasma Proteome Dynamics with 2H2O and Liquid Chromatography Tandem Mass Spectrometry", Analytical Biochemistry, vol. 420, 2012, pp. 73-83.
Szymanski et al., "Beyond the Proteome: Non-Coding Regulatory RNAs", Genome Biology, vol. 3, No. 5, Apr. 15, 2002, pp. 1-8.
Hellerstein et al., "Model for Measuring Absolute Rates of Hepatic de Novo Lipogenesis and Reesterification of Free Fatty Acids", The American Journal of Physiology, vol. 265, 1993, pp. E814-E820.
Hellerstein et al., "Subpopulations of Long-Lived and Short-Lived T Cells in Advanced HIV-1 Infection", The Journal of Clinical Investigation, vol. 112, No. 6, 2003, pp. 956-966.
Hellerstein et al., "T Cell Turnover in HIV-1 Disease", Immunity, vol. 7, 1997, pp. 583-589.
Hellerstein, M. K., "Carbohydrate-Induced Hypertriglyceridemia: Modifying Factors and Implications for Cardiovascular Risk", Curr. Opin. Lipidology, vol. 13, 2002, pp. 33-40.
Hellerstein, M. K., "Measurement of T-Cell Kinetics: Recent Methodologic Advances", Trends Immunology Today, vol. 20, No. 10, 1999, pp. 438-441.
Hellerstein, M. K., "Methods for Measurement of Fatty Acid and Cholesterol Metabolism", Current Opinion in Lipidology,vol. 6, 1995, pp. 172-181.
International Written Opinion received for PCT Patent Application No. PCT/US2012/068068, mailed on Feb. 8, 2013, 5 pages.
Hellerstein, M. K., "No Common Energy: de Novo Lipogenesis as the Road Less Traveled", The American Journal of Clinical Nutrition, vol. 74, 2001, pp. 707-708.
Hellerstein, M. K., "Synthesis of Fat in Response to Alterations in Diet: Insights from New Stable Isotope Methodologies", Lipids, vol. 31 (Supp), 1996, pp. S117-S125.

Hellerstein, M. K., "The Changing Face of AIDS: Translators Needed", The American Journal of Clinical Nutrition, vol. 70, 1999, pp. 787-788.
Hellerstein, Marc K., "In Vivo Measurement of Fluxes Through Metabolic Pathways: The Missing Link in Functional Genomics and Pharaceutical Research", Annu. Rev. Nutr., vol. 3, 2003, pp. 379-402.
Ho et al., "Rapid Turnover of Plasma Virions and CD4 Lymphocytes in HIV-1 Infection", Nature, vol. 373, 1995, pp. 123-126.
Hoh et al., "De Novo Lipogenesis Predicts Short-Term Body-Composition Response by Bioelectrical Impedance Analysis to Oral Nutritional Supplements in HIV-Associated Wasting", The American Journal of Physiology, vol. 68, 1998, pp. 154-163.
Hsieh et al., "Dynamics of Keratinocytes in Vivo Using 2H2O Labeling: A Sensitive Marker of Epidermal Proliferation State", J Invest Dermatol, vol. 123, 2004, pp. 530-536.
Hudgins et al., "Human Fatty Acid Synthesis is Stimulated by a Eucaloric Low Fat, High Carbohydrate Diet", J. Clin. Invest., vol. 97, No. 9, 1996, pp. 2081-2091.
Hudgins et al., "Relationship Between Carbohydrate-Induced Hypertriglyceridemia and Fatty Synthesis in Lean and Obese Subjects", J. Lipid Res., vol. 41, 2000, pp. 595-604.
Hulzebos et al., "Measurement of Parameters of Cholic Acid Kinetics in Plasma using a Microscale Stable Isotope Dilution Technique: Application to Rodents and Humans", Journal of Lipid Research, vol. 42, 2001, pp. 1923-1929.
Humphrey et al., "A New Method for the Measurement of Protein Turnover", Biochem. J., vol. 148, 1975, pp. 119-127.
Humphrey et al., "A Sensitive Method for Measuring Protein Turnover Based on the Measurement of 2-3H-labeled Amino Acids in Proteins", Biochem. J., vol. 156, 1976, pp. 561-568.
Iyengar et al., "Human Stools as a Source of Viable Colonic Epithelial Cells", The FASEB Journal, vol. 5, 1991, pp. 2856-2859.
James, J. S., "Clinical Implications of Virological Failure: Interview with Steven Deeks, M.D., San Francisco General Hospital", AIDS Treatment News, vol. 289, 1998, pp. 6-7.
Jennings et al., "The Use of Infrared Spectrophotometry for Measuring Body Water Spaces", Clinical Chemistry, vol. 45, No. 7, Jul. 1999, pp. 1077-1081.
Jones et al., "An Integrated 2H and 13C NMR Study of Gluconeogenesis and TCA Cycle Flux in Humans", American Journal of Physiology-Endocrinology and Metabolism, vol. 281, 2001, pp. E848-E856.
Jones et al., "Evidence for Diurnal Periodicity in Human Cholesterol Synthesis", Journal of Lipid Research, vol. 31, 1990, pp. 667-673.
Jung et al., "Metabolic Adaptations to Dietary Fat Malabsorption in Chylomicron-Deficient Mice", Biochem. J., vol. 343, 1999, pp. 473-478.
Jungas, "Fatty Acid Synthesis in Adipose Tissue Incubated in Tritiated Water", Biochemistry, vol. 7, No. 10, 1968, pp. 3708-3717.
Katz, "Futile Cycles in the Metabolism of Glucose", Curr. Top Cell Regul., vol. 10, 1976, pp. 237-289.
Kelleher et al., "Model Equations for Condensation Biosynthesis Using Stable Isotopes and Radioisotopes", Am. J. Physiol., vol. 262, 1992, pp. E118-E125.
Khairallah et al., "Assessment of Protein Turnover in Perfused Rat Liver: Evidence for Amino Acid Compartmentation from Differential Labeling of Free and tRNA-bound Valine", J Biol Chem, vol. 251, No. 5, 1976, pp. 1375-1384.
Kim et al., "A New Stable Isotope-Mass Spectrometric (MS) Method to Measure Proliferation Rates of Colon Epithelial Cells", Faseb Journal, vol. 14, No. 4, 2000, p. A718.
Lammert et al., "Effects of Isoenergetic Overfeeding of Either Carbohydrate or Fat in Young Men", British Journal of Nutrition, vol. 84, 2000, pp. 233-245.
Lee, "Cardiorespiratory Fitness, Body Composition, and All-Cause and Cardiovascular Disease Mortality in Men 1-3", Am. J. Clin. Nutr., vol. 69, 1999, pp. 373-380.
Lefebvre, "Naturally Labeled 13C-Glucose: A New Tool to Measure Oxidation Rates of Exogenous Glucose", Diabetes, vol. 28 (Suppl. 1), Jan. 1979, pp. 63-65.
Leung et al., "A Deficiency of Microsomal Triglyceride Transfer Protein Reduces Apolipoprotein B Secretion", The Journal of Biological Chemistry, vol. 275, No. 11, 2000, pp. 7515-7520.

(56) References Cited

OTHER PUBLICATIONS

Lewanczuk et al., "Comparison of the [13 C] Glucose Breath Test to the Hyperinsulinemic-Euglycemic Clamp When Determining Insulin Resistance", Diabetes Care, vol. 27, No. 2, 2004, pp. 441-447.
Lipkin, "Cell Proliferation Kinetics in the Gastrointestinal Tract of Man. I. Cell Renewal in Colon and Rectum", Journal of Clinical Investigations, vol. 42, No. 6, 1963, pp. 767-776.
Lipkin, "Proliferation and Differentiation of Normal and Diseased Gastrointestinal Cells", In Physiology of the Gastrointestinal Tract, L.R. Johnson ed., Raven Press, New York, 1987, pp. 255-284.
Lutton et al., "Critical analysis of the Use of 14C-acetate for Measuring In Vivo Rat Cholesterol Synthesis", Reprod. Nutr. Dev., vol. 30, 1990, pp. 71-84.
Macallan et al., "Measurement of Cell Proliferation by Labeling of DNA with Stable Isotope-Labeled Glucose: Studies in Vitro, in Animals, and in Humans", Proc. Natl. Acad. Sci., vol. 95, 1998, pp. 708-713.
Maentausta et al., "Radioimmunoassay of Conjugated Cholic Acid, Chenodeoxycholic Acid, and Deoxycholic Acid from Human Serum, with Use of 125l-Labeled Ligands", Clin. Chem., vol. 25, No. 2, 1979, pp. 264-268.
Malberg et al., "Chronic Antidepressant Treatment Increases Neurogenesis in Adult Rat Hippocampus", The Journal of Neuroscience, vol. 20, No. 24, Dec. 15, 2000, pp. 9104-9110.
Margolick et al., "Failure of T-cell Homeostasis Preceding AIDS in HIV-1 Infection", Nature Medicine, vol. 1, No. 7, 1995, pp. 674-680.
Maric et al., "Functional Ionotropic Glutamate Receptors Emerge During Terminal Cell Division and Early Neuronal Differentiation of Rat Neuroepithelial Cells", Journal of Neuroscience Research, vol. 61, No. 6, 2000, pp. 652-662.
Marin et al., "Dynamic Profiling of the Glucose Metabolic Network in Fasted Rat Hepatocytes using [1,2-13C2] Glucose", Biochemical Journal, vol. 381, 2004, pp. 287-294.
Martin et al., "Discovery of a Human Liver Glycogen Phosphorylase Inhibitor That Lowers Blood Glucose in Vivo", Proc. Natl. Acad. Sci. USA, vol. 95, No. 4, 1998, pp. 1776-1781.
Mathur-De Vre et al., "Molecular Aspects of Tritiated Water and Natural Water in Radiation Biology", Prog. Biophys. Molec. Biol., vol. 43, 1984, pp. 161-193.
McCloskey, James A., "ElectronIonization Mass Spectra of Trimethylsilyl Derivatives of Nucleosides", Meth. Enz., vol. 193, 1990, pp. 825-841.
McCune et al., "Factors Influencing T-Cell Turnover in HIV-1-Seropositive Patients", J. Clin. Invest., vol. 105, 2000, pp. R1-R8.
McCune, J. M., "Thymic Function in HIV-1 Disease", Seminars in Immunology, vol. 9, 1997, pp. 397-404.
McFarland et al., "Inhibition of DNA Synthesis in Neonatal Rat Brain Regions Caused by Acute Nicotine Administration", Developmental Brain Research, vol. 58, No. 2, Feb. 22, 1991, pp. 223-229.
McLean et al., "In Vivo Estimates of Division and Death Rates of Human T Lymphocytes", Proc. Natl. Acad. Sci USA, vol. 92, 1995, pp. 3707-3711.
Meier et al., "Rates of Protein Synthesis and Turnover in Fetal Life", Am J Physiol., vol. 240, No. 3, 1981, pp. E320-E324.
Mellors et al., "Prognosis in HIV-1 Infection Predicted by the Quantity of Virus in Plasma", Science, vol. 272, 1996, pp. 1167-1170.
Mellors et al., "Quantitation of HIV-1 RNA in Plasma Predicts Outcome after Seroconversion", Ann. Intern. Med., vol. 122, 1995, pp. 573-579.
Messmer et al., "In Vivo Measurements Document the Dynamic Cellular Kinetics of Chronic Lymphocytic Leukemia B Cells", J. Clin. Invest., vol. 115, Feb. 10, 2005, pp. 755-764.
Mewissen et al., "Comparative Incorporation of Tritium from Tritiated Water Versus Tritiated Thymidine, Uridine or Leucine", Curr. Top Rad. Res. Quart., vol. 12, 1977, pp. 225-254.
Michie et al., "Lifespan of Human Lymphocyte Subsets Defined by CD45 Isofomis,", Nature, vol. 360, 1992, pp. 264-265.
Mikkola et al., "Serum Cholesterol Efflux Potential is an Independent Predictor of Coronary Artery Atherosclerosis", Atherosclerosis, vol. 170, 2003, pp. 31-38.
Mindham et al., "Application of Simultaneous Spleen and Liver Perfusion to the Study of Reverse Cholesterol Transport", Biochemical Journal, vol. 302, 1994, pp. 207-213.
Misell et al., "A new in Vivo Stable Isotope Method for Measuring Mammary Epithelial Cell Proliferation", Faseb Journal Experimental Biology, vol. 14, No. 4, 2000, p. 550.
Mohri et al., "Increased Turnover of T Lymphocytes in HIV-1 Infection and its Reduction by Antiretroviral Therapy", J. Exp. Med., vol. 194, No. 9, 2001, pp. 1277-1287.
Morris et al., "Evidence that a Slowly Cycling Subpopulation of Adult Murine Epidermal Cells Retains Carcinogen", Cancer Research, vol. 46, 1997, pp. 3061-3066.
Morris et al., "Evidence that Cutaneous Carcinogen-Initiated Epithelial Cells from Mice are Quiescent Rather than Actively Cycling", Cancer Research, vol. 57, 1997, pp. 3436-3443.
Morsches et al., "Tierexperimentelle Untersuchungen Uber Die Beziehungen Zwischen Der Hydroxyprolinausscheidung Im Urin Und Den Hydroxyprolinfraktionen Im Serum", Der Hautarzt, vol. 27, 1976, pp. 234-242.
Mosier, D. E., CD4.sup.+ Cell Turnover, Nature, vol. 375, 1995, pp. 193-194.
Murali-Krishna et al., "Counting Antigen-Specific CD8 T Cells: A Reevaluation of Bystander Activation during Viral Infection", Immunity, vol. 8, 1998, pp. 177-187.
Nagasaka et al., "Endogenous Glucose Production and Glucose Effectiveness in Type 2 Diabetic Subjects Derived From Stable-Labeled Minimal Modal Approach", Diabetes, vol. 48, May 1999, pp. 1054-1056.
Naik et al., "Pharmacological Activation of Liver X Receptors Promotes Reverse Cholesterol Transport in Vivo", Circulation, vol. 113, 2006, pp. 90-97.
Nanjee et al., "Intravenous apoA-I/lecithin Discs Increase Pre-Beta-HDL Concentration in Tissue Fluid and Stimulate Reverse Cholesterol Transport in Humans", Journal of Lipid Research, vol. 42, 2001, pp. 1586-1593.
Neese et al., "Advances in the Stable Isotope-Mass Spectrometric Measurement of DNA Synthesis and Cell Proliferation", Analytical Biochemistry, vol. 298, No. 2, 2001, pp. 189-195.
Neese et al., "Gluconeogenesis and Intrahepatic Triose Phosphate Flux in Response to Fasting or Substrate Loads", Journal of Biological Chemistry, vol. 270, No. 24, 1995, pp. 14452-14463.
Neese et al., "Measurement of Endogenous Synthesis of Plasma Cholesterol in Rats and Humans Using MIDA", Am. J. Physiol., vol. 264, 1993, pp. E139-E147.
Neese et al., "Measurement in Vivo of Proliferation Rates of Slow Turnover Cells by 2H2O Labeling of the Deoxyribose Moiety of DNA", Proceedings of the National Academy of Sciences, vol. 99, No. 24, Nov. 26, 2002, pp. 15345-15350
Ong et al., "Stable Isotope Labeling by Amino Acids in Cell Culture, SILAC, as a Simple and Accurate Approach to Expression Proteomics", Molecular and Cellular Proteomics, vol. 1, 2002, pp. 376-386.
Oshima et al., "COX Selectivity and Animal Models for Colon Cancer", Current Pharmaceutical Design, vol. 8, 2002, pp. 1021-1034.
Ouguerram et al., "A New Labeling Approach Using Stable Isotopes to Study In Vivo Plasma Cholesterol Metabolism in Humans", Metabolism, vol. 51, No, 1, Jan. 2002, pp. 5-11.
Oyaizu et al., "Role of Apoptosis in HIV Disease Pathogenesis", J. of Clinical Immunology, vol. 15, No. 5, 1995, pp. 217-231.
Paku, S. "Origin and Structural Evolution of the Early Proliferating Oval Cells in Rat Liver", American Journal of Pathology, vol. 158, No, 4, Apr. 2001, pp. 1313-1323.
Palmer et al., Telomere Length, Telomerase Activity, and Replicative Potential in HIV Infection: Analysis of CD4+ and CD8+ T Cells from HIV-discordant Monozygotic Twins, J. Experimental Medicine, vol. 185, No. 7, 1997, pp. 1381-1386.
Panteleo, Giuseppe. "Unraveling the Strands of HIV's Web", Nature Medicine, vol. 5, No. 1, 1999, pp. 27-28.
Papageorgopoulos et al., "Measuring Protein Synthesis by Mass Isotopomer Distribution Analysis (MIDA)", Analytical Biochemistry, vol. 267, 1999, pp. 1-16.
Papageorgopoulos et al., "Toward the Measurement of Protein Synthesis by Mass Isotopomer Distribution Analysis (MIDA):Resolution of Isotopomers in a [d.sub.3 ]-Leucine Enriched Synthetic

(56) References Cited

OTHER PUBLICATIONS

Oligopeptide Using Electrospray/Quadrupole Mass Spectrometry (ESI/MS)", Federation of American Societies for Experimental Biology, vol. 1022, 1993, p. A177.
Park et al., "Measurement of Small Intestinal Cell Turnover with [6,6, 2H2] Glucose", Berkeley Scientific, Abstract, vol. 1, No. 2, 1997, pp. 41-43.
Parks et al., "Carbohydrate-induced Hypertriacylglycerolemia: Historical Perspective and Review of Biological Mechanisms", Am. J. Nutr., vol. 71, 2000, pp. 412-433.
Parks et al., "Dependence of Plasma a-Tocopherol Flux on Very Low-Density Triglyceride Clearance in Humans", Free Radical Biology & Medicine, vol. 29, No. 11, 2000, pp. 1151-1159.
Parks et al., "Effects of a Low-Fat, High-Carbohydrate Diet on VLDL-Triglyceride Assembly, Production, and Clearance", J. Clin. Invest. vol. 104, No. 8, 1999, pp. 1087-1096.
Paša-Tolic et al., "High Throughput Proteome-Wide Precision Measurements of Protein expression Using Mass Spectrometry", J. Am. Chem. Soc., vol. 121, 1999, pp. 7949-7950.
Patsalos et al., "Pattern of Myelin Breakdown During Sciatic Nerve Wallerian Degeneration: Reversal of the Order of Assembly", The Journal of Cell Biology, vol. 87, 1980, pp. 1-5.
Patterson et al., "Concentration Dependence of Methyl-Palmitate Isotope Ratios by Electron Impact Ionization Gas Chromatography/Mass Spectrometry", Biol. Mass Spectrom., vol. 22, 1993, pp. 481-486.
Patterson et al., "Measurement of Very Low Stable Isotope Enrichments by Gas Chromatography/Mass Spectrometry: Application to Measurement of Muscle Protein Synthesis", Metabolism, vol. 46, No. 8, Aug. 1997, pp. 943-948.
Patton et al., "Measurements of Fatty Acid Synthesis by Incorporation of Deuterium from Deuterated Water", Biochemistry, vol. 18, No. 14, 1979, pp. 3186-3188.
Perelson et al., "Decay Characteristics of HIV-1-Infected Compartments During Combination Therapy", Nature 387, 1997, pp. 188-191.
Perelson et al., "HIV-1 Dynamics in Vivo: Virion Clearance Rate, Infected Cell Life-Span, and Viral Generation Time", Science, vol. 271, 1996, pp. 1582-1586.
Perochon et al., "Radiolabeling of the Lipids of Chinese Hamster Ovary Cells with the Probe [3-(Trifluoromethyl)-3-(m-125]iodophenyl)diazinne", Analytical Biochemistry, vol. 254, 1997, pp. 109-118.
Previs et al., "Estimation of Protein Turnover in Vivo Using D2O", Diabetes Abstract Book, 61st Scientific Sessions, vol. 50, Supplement 2, A301, 2001, 1248-p.
Propper et al., "Use of Positron Emission Tomography in Pharmacokinetic Studies to Investigate Therapeutic Advantage in a Phase I Study of 120-Hour Intravenous Infusion XR5000", Journal of Clinical Oncology, vol. 21, No. 2, Jan. 2003, pp. 203-210.
Ramakers et al., "Chronic Suppression of Bioelectric Activity and Cell Survival in Primary Cultures of Rat Cerebral Cortex Biochemical Observations", European Journal of Neuroscience, vol. 3, No. 2, 1991, pp. 154-161.
Ravichandran et al., "In Vivo Labeling Studies on the Biosynthesis and Degradation of Collagen in Experimental Myocardial Infarction", Biochemistry Journal, vol. 24, No. 3, 1991, pp. 405-414.
Reichard, P., "From Deoxynucleotides to DNA Synthesis", Federation Proceedings, vol. 37, No. 1, 1978, pp. 9-14.
Reichard, P., "Interactions Between Deoxyribonucleotide and DNA Synthesis", Ann. Rev. Biochem. vol. 57, 1988, pp. 349-374.
Eriksson et al., "Stimulation of Fecal Steroid Excretion After Infusion of Recombinant Proapolipoprotein A-1: Potential Reverse Cholesterol Transport in Humans", Circulation, vol. 100, 1999, pp. 594-598.
International Preliminary Report on Patentability received for PCT Patent Application No. PCT/US2012/054329, mailed on Mar. 20, 2014, 11 pages.

International Search Report and Written Opinion received for PCT Patent Application No. PCT/US2012/054329, mailed on Dec. 7, 2012, 13 pages.
International Preliminary Report on Patentability received for PCT Patent Application No. PCT/US2012/068068, mailed on Jun. 19, 2014, 7 pages.
International Search Report received for PCT Patent Application No. PCT/US2012/068068, mailed on Feb. 8, 2013, 3 pages.
International Search Report & Written Opinion received for PCT Patent Application No. PCT/US2014/042186, mailed on Oct. 1, 2014, 10 pages.
Carling et al., "Simultaneous Determination of Guanidinoacetate, Creatine and Creatinine in Urine and Plasma by Un-Derivatized Liquid Chromatography-Tandem Mass Spectrometry", Annals of Clinical Biochemistry, vol. 45, 2008, pp. 575-584.
Clark et al., "Total Body Skeletal Muscle Mass: Estimation by Creatine (methyl-d3) Dilution in Humans.", Journal of Applied Physiology, vol. 116, No. 12, Jun. 15, 2014, pp. 1605-1613.
Heymsfield et al., "Measurement of Muscle Mass in Humans: Validity of the 24-hour Urinary Creatinine Method", American Journal of Clinical Nutrition, vol. 37, Mar. 1983, pp. 478-494.
Kreisberg et al., "Measurement of Muscle Mass in Humans by Isotopic Dilution of Creatine-14C", Journal of Applied Physiology, vol. 28, No. 3, Mar. 1970, pp. 264-267.
Mussini et al., "Determination of Creatine in Body Fluids and Muscle", Journal of Chromatography Biomedical Applications, vol. 305, 1984, pp. 450-455.
Picou et al., "The Measurement of Muscle Mass in Children Using [15N] Creatine", Pediatric Research, vol. 10, 1976, pp. 184-188.
Poortmans et al., "Estimation of Total-Body Skeletal Muscle Mass in Children and Adolescents", Medicine & Science in Sports & Exercise, vol. 37, 2005, pp. 316-322.
Reeds et al., "Muscle Mass and Composition in Malnourished Infants and Children and Changes Seen after Recovery", Pediatric Research, vol. 12, 1978, pp. 613-618.
Schutte et al., "Total Plasma Creatinine: An Accurate Measure of Total Striated Muscle Mass", The American Physiological Society, vol. 51, 1981, pp. 762-766.
Smith-Palmer, Truis, "Separation Methods Applicable to Urinary Creatine and Creatinine", Journal of Chromatography B, vol. 781, 2002, pp. 93-106.
Stimpson, et al., "Longitudinal changes in total body creatine pool size and skeletal muscle mass using the D3-creatine dilution methods", Journal of Cachexia, Sarcopenia and Muscle, vol. 4, No. 3, Jun. 25, 2013, pp. 217-223.
Stimpson et al., "Longitudinal Determination of Total Body Creatine Pool Size and Skeletal Muscle Mass in Rats by D3-Creatine Dilution", The FASEB Journal, vol. 27, Apr. 1, 2013, p. 1b410.
Stimpson et al., "Total-Body Creatine Pool Size and Skeletal Muscle Mass Determination by Creatine-(methyl-d3) Dilution in Rats", Journal of Applied Physiology, vol. 112, No. 11, Mar. 15, 2012, pp. 1940-1948.
Wang et al., "Total-Body Skeletal Muscle Mass: Evaluation of 24-h Urinary Creatinine Excretion by Computerized Axial Tomography", American Society for Clinical Nutrition, vol. 63, 1996, pp. 863-869.
Wang et al., "Urinary Creatinine-Skeletal Muscle Mass Method: A Prediction Equation Based on Computerized Axial Tomography1-3", Biomedical and Environmental Sciences, vol. 9, 1996, pp. 185-190.
Welle et al., "Utility of Creatinine Excretion in Body-Composition Studies of Healthy Man and Women Older than 60 y1-3", The American Journal of Clinical Nutrition, vol. 63, Feb. 1996, pp. 151-156
Wells et al., "Body Composition by 2H Dilution in Gambian Infants: Comparison with UK Infants and Evaluation of Simple Prediction Methods", The British Journal of Nutrition, vol. 102, 2009, pp. 1776-1782.
Abramson Hanley N., "The Lipogenesis Pathway as a Cancer Target", Journal of Medicinal Chemistry, vol. 54, 2011, pp. 5615-5638.
Ackerstaff et al., "Choline Phospholipid Metabolism: A Target in Cancer Cells?", Journal of Cellular Biochemistry, vol. 90, Issue 3, Oct. 2003, pp. 525-533.
Baran et al., "Mass Spectrometry based Metabolomics and Enzymatic Assays for Functional Genomics", Current Opinion in Microbiology, vol. 12, No. 5, 2009, pp. 547-552.

(56) References Cited

OTHER PUBLICATIONS

Bartella et al., "Proton MR Spectroscopy with Choline Peak as Malignancy Marker Improves Positive Predictive Value for Breast Cancer Diagnosis: Preliminary Study", Radiology, vol. 239, No. 3, Jun. 2006, pp. 686-692.

Bertos et al., "Breast Cancer- One Term, Many Entities?", The Journal of Clinical Investigation, vol. 121, No. 10, 2011, pp. 3789-3796.

Bougnoux et al., "Fatty Acids and Breast Cancer: Sensitization to Treatments and Prevention of Metastatic Re-Growth", Progress Lipid Research, vol. 49, Issue 1, Jan. 2010, pp. 76-86.

Bowen et al., "Dealing with the Unknown: Metabolomics and Metabolite Atlases", Journal of American Society of Mass Spectrometry, vol. 21, 2010, pp. 1471-1476.

Busch et al "Measurement of Protein Turnover Rates by Heavy Water Labeling of Nonessential Amino Acids", Biochimica et Biophysica Acta, vol. 1760, 2006, pp. 730-744.

Chen et al., "Application of Probe Electrospray to Direct Ambient Analysis of Biological Samples", Rapid Commun Mass Spectrom, vol. 22, 2008, pp. 2366-2374.

Cichon et al., "Microenvironmental Influences that Drive Progression from Benign Breast Disease to Invasive Breast Cancer", J. Mammary Gland Biol Neoplasia, vol. 15, 2010, pp. 389-397.

Commerford et al., "The Distribution of Tritium Among the Amino Acids of Proteins Obtained from Mice Exposed to Tritiated Water", Radiation Research, vol. 94, 1983, pp. 151-155.

Cornett et al., "MALDI Imaging Mass Spectrometry: Molecular Snapshots of Biochemical Systems", Nature Methods, vol. 4, No. 10, Oct. 2007, pp. 828-833.

Deberardinis et al., "Brick by Brick: Metabolism and Tumor Cell Growth", Current Opinion in Genetics & Development, vol. 18, No. 1, Feb. 2008, pp. 54-61.

Deberardinis et al., "The Biology of Cancer: Metabolic Reprogramming Fuels Cell Growth and Proliferation", Cell Metabolism, vol. 7, Jan. 2008, pp. 11-20.

Deeb et al., "Identification of an Integrated SV40 Tit-antigen Cancer Signature in Gressive Human Breast, Prostate, and Lung Carcinomas with Poor Prognosis", Cancer Research, vol. 67, No. 17, 2007, pp. 8065-8080.

Diraison et al., "In Vivo Measurement of Plasma Cholesterol and Fatty Acid Synthesis with Deuterated Water: Determination of the Average Number of Deuterium Atoms Incorporated. Metabolism", Metabolism: Clinical and Experimental, vol. 45, No. 7, Jul. 1996, pp. 817-821.

Dowsett et al., "Assessment of Ki67 in Breast Cancer. Recommendations From The International Ki67 in Breast Cancer Working Group", Journal of the National Cancer Institute, vol. 103, 2011, pp. 1656-1664.

Gerlinger et al., "Intratumor Heterogeneity and Branched Evolution Revealed by Multiregion Sequencing", The New England Journal of Medicine, vol. 366, No. 10, 2012, pp. 883-892.

Green et al., "The C3(1)/SV40 T-Antigen Transgenic Mouse Model of Mammary Cancer: Ductal Epithelial Cell Targeting with Multistage Progression to Carcinoma", Oncogene, vol. 19, 2000, pp. 1020-1027.

Guillermet-Guibert et al., "Targeting the Sphingolipid Metabolism to Defeat Pancreatic Cancer Cell Resistance to the Chemotherapeutic Gemcitabine Drug", Molecular Cancer Therapeutics, vol. 8, No. 4, Apr. 2009, pp. 809-821.

Hanahan et al., "Hallmarks of Cancer: The Next Generation", Cell, vol. 144, 2011, pp. 646-674.

Nankin et al., "The Relationship between MALDI IMS Intensity and Measured Quantity of Selected Phospholipids in Rat Brain Sections", Anal Chemistry, vol. 82, No. 20, 2010, pp. 8476-8484.

Hellerstein et al., "Measurement of De Novo Hepatic Lipogenesis in Humans Using Stable Isotopes", Journal of Clinical Investigation, vol. 87, May 1991, pp. 1841-1852.

Herschkowitz et al., "The Functional Loss of the Retinoblastoma Tumour Suppressor is a Common Event in Basal-Like and Luminal B Breast Carcinomas", Breast Cancer Research, vol. 10, 2008, 13 pages.

Hilvo et al., "Novel Theranostic Opportunities Offered by Characterization of Altered Membrane Lipid Metabolism in Breast Cancer Progression", Cancer Research, vol. 71, 2011, pp. 3236-3245.

Hsu et al., "Cancer Cell Metabolism: Warburg and Beyond", Cell, vol. 134, Sep. 5, 2008, pp. 703-707.

Igal, R. Ariel., "Stearoyl-CoA Desaturase-1: A Novel Key Player in the Mechanisms of Cell Proliferation, Programmed Cell Death and Transformation to Cancer", Carcinogenesis, vol. 31, No. 9, 2010, pp. 1509-1515.

Boros et al., "Metabolic Profiling of Cell Growth and Death in Cancer: Applications in Drug Discovery", Drug Discovery Today, vol. 7, No. 6, Mar. 2002, pp. 364-372.

Bravo et al., "Decreased Hepatic Uptake and Processing of High Density Lipoprotein Unesterified Cholesterol and Cholesteryl Ester with Age in the Rat", Journal of Biochemistry, vol. 116, 1994, pp. 1088-1095.

Brown et al., "Treating Patients with Documented Atherosclerosis to National Cholesterol Education Program-Recommended Low-Density-Lipoprotein Cholesterol Goals with Atorvastatin, Flufastatin, Lovastatin and Simvastatin", Journal of the American College of Cardiology, vol. 32, 1998, pp. 665-672.

Bucy et al., "Analysis of Lymph Node Biopsies in HIV Infected Patients Beford and After HAART", 5th Conference on Retroviruses and Opportunistic Infections, Session 66, vol. 519, 1998, 177 Pages (Abstract only).

Caldwell et al., "Quantification of Peptide Isotopomer Abundances and Determination of Protein (sic) Turnover Rates by Using Mass Isotopomer Distribution Analysis", 41st Annual Amer. Society Mass Spectrometry on Mass Spectrometry, 1993, p. 331a (Abstract only).

Cassella et al., "Mechanisms of Lymphocyte Killing by HIV", Current Opinion in Hematology, vol. 4, 1997, pp. 24-31.

Cesar et al., "Direct Measurement of CD4+ and CD8+ T Cell Proliferation Rates in Vivo in AIDS Patients Using a Stable Isotope-Mass Spectrometric Technique", 5th Conference on Retroviruses and Opportunistic Infections, Chicago Illinois, 1998, Abstract only.

Chinkes et al., "Comparison of Mass Isotopomer Dilution Methods Used to Compute VLDL Production In Vivo", The American Journal of Physiology, vol. 271, 1996, pp. E373-E383.

Christiansen et al., "Effect of Dietary Energy Restriction on Glucose Production and Substrate Utilization in Type 2 Diabetes", Diabetes, vol. 49, Oct. 2000, pp. 1691-1699.

Clarke, R. B., "Isolation and Characterization of Human Mammary Stem Cells", Cell Proliferation, vol. 38, 2005, pp. 375-386.

Clayton, "Replication and Transcription of Vertebrate Mitochondrial DNA", Annual Review of Cell Biology, vol. 7, 1991, pp. 453-478.

Cohen et al., "Purine and Pyrimidine Metabolism in Human T Lymphocytes. Regulation of Deoxyribonucleotide Metabolism", The Journal of Biological Chemistry, vol. 258, No. 20, 1983, pp. 12334-12340.

Cohen, J. "Failure Isn't What it Used to be . . . But Neither is Success", Science, vol. 279, 1998, pp. 1133-1134.

Collins et al., "A Method for Measuring Mitochondrial Proliferation In Vivo Using 2H20 Incorporation Into Mitochondria DNA", FASEB Journal, vol. 14, No. 4, Mar. 15, 2000, p. A620.

Collins et al., "Measurement of Mitochondrial DNA Synthesis In Vivo Using a Stable Isotope-Mass Spectrometric Technique", Journal of Applied Physiology, vol. 94, 2003, pp. 2203-2211.

Connors et al., "HIV Infection Induces Changes in CD4+ T-Cell Phenotype and Depletions Within the CD4+ T-Cell Repertoire that are Not Immediately Restored by Antiviral or Immune-Based Therapies", Nature Medicine, vol. 3, 1997, pp. 533-540.

Conrads et al., "Stable Isotope Labeling in Proteomics", The Synthesis Cambridge Isotope Laboratories, vol. 3, No. 2, Jan. 2002, pp. 1-3.

Craig et al., "The Impact of Physical Activity on Lipids, Lipoproteins, and Blood Pressure in Preadolescent Girls", Pediatrics, vol. 98, 1996, pp. 389-395.

Crain, "Preparation and Enzymatic Hydrolysis of DNA and RNA for Mass Spectrometry", Methods in Enzymology, vol. 193, 1990, pp. 782-790.

Dalvie, D. "Recent Advances in the Applications of Radioisotopes in Drug Metabolism, Toxicology and Pharmacokinetics", Current Pharmaceutical Design, vol. 6, 2000, pp. 1009-1028.

(56) References Cited

OTHER PUBLICATIONS

Davis et al., "Effect of Pinitol Treatment on Insulin Action in Subjects with Insulin Resistance", Diabetes Care, vol. 23, No. 7, Jul. 2000, pp. 1000-1005.

Deeks et al., "CD4+ T Cell Kinetics and Activation in Human Immunodeficiency Virus-Infected Patients who Remain Viremic Despite Long-Term Treatment with Protease Inhibitor-Based Therapy", The Journal of Infectious Diseases, vol. 185, Feb. 1, 2002, pp. 315-323.

Deeks et al., "Viral Load and CD4+ T Cell Changes in Patients Failing Potent Protease Inhibitor Therapy", 5th Conference on Retroviruses and Opportunistic Infections, Session 53, vol. 419, 1998, p. 158 (Abstract only).

Dekker et al., "Glucose Homeostasis in Children with Falciparum Malaria: Precursor Supply Limits Gluconeogenesis and Glucose Production", J. Clin. Endocrinol. Metabol., vol. 82, 1997, pp. 2514-2521.

Di Buono et al., "Comparison of Deuterium Incorporation and Mass Isotopomer Distribution Analysis for Measurement of Human Cholesterol Biosynthesis", Journal of Lipid Research, vol. 41, 2000, pp. 1516-1523.

Dimitrov et al., "Scientific Correspondence", Nature, vol. 375, 1995, pp. 194-195.

Emken, E. A., "Metabolism of Dietary Stearic Acid Relative to Other Fatty Acids in Human Subjects", The American Journal of Clinical Nutrition, vol. 60, (Suppl), 1994, pp. 1023S-1028S.

Emken et al., "Incorporation of Deuterium-Labeled Trans- and CIS-13-Octadeconoic Acids in Human Plasma Lipids", Journal of Lipid Research, vol. 24, 1983, pp. 34-41.

Etnier et al., "Metabolism of Organically Bound Tritium in Man", Radiation Research, vol. 100, 1984, pp. 487-502.

Fagerquist et al., "Elimination of the Concentration Dependence in Mass Isotopomer Abundance Mass Spectrometry of Methyl Palmitate Using Metastable Atom Bombardment", Journal of the American Society of Mass Spectrometry, vol. 12, 2001, pp. 754-761.

Fagerquist et al., "Molecular Ion Fragmentation and its Effects on Mass Isotopomer Abundances of Fatty Acid Methyl Esters Ionized by Electron Impact", Journal of the American Society of Mass Spectrometry, vol. 10, 1999, pp. 430-439.

Gasparini et al., "Amplification of DNA from Epithelial Cells in Urine", The New England Journal of Medicine, vol. 320, No. 12, 1989, p. 809.

Gerling et al., "Prediction of Liver Fibrosis According to Serum Collagen VI Level in Children with Cystic Fibrosis", The New England Journal of Medicine, vol. 336, No. 22, 1997, pp. 1611-1612.

Gorochov et al., "Perturbation of CD4+ and CD8+ T-Cell Repertoires During Progression to AIDS and Regulation of the CD4+ Repertoire During Antiviral Therapy", Nature Medicine, vol. 4, 1998, pp. 215-221.

Goz, "The Effects of Incorporation of 5-Halogenated Deoxyuridines into the DNA of Eukaryotic Cells", Pharmacological Reviews, vol. 29, 1977, pp. 249-272.

Gratzner, "Monoclonal Antibody to 5-Bromo- and 5-Iododeoxyuridine: A New Reagent for Detection of DNA Replication", Science, vol. 218, 1982, pp. 474-475.

Guo et al., "De Novo Lipogenesis in Adipose Tissue of Lean and Obese Women: Application of Deuterated Water and Isotope Ratio Mass Spectrometry", International Journal of Obesity and Related Metabolic Disorders, vol. 24, 2000, pp. 932-937.

Gygi et al., "Using Mass Spectrometry for Quantitative Proteomics", Proteomics: A Trends Guide, 2000, pp. 31-36.

Hansen et al., "A Practical Method for Uniform Isotopic Labeling of Recombinant Proteins in Mammalian Cells", Biochemistry, vol. 31, 1992, pp. 12713-12718.

Heck et al., "Posttranslational Amino Acid Epimerization: Enzyme-Catalyzed Isomerization of Amino Acid Residues in Peptide Chains", Proceedings of the National Academy of Sciences of the United States of America, vol. 93, Apr. 1996, pp. 4036-4039.

Hellerstein, "Mass Isotopomer Distribution Analysis: A Technique for Measuring Biosynthesis and Turnover of Polymers", The American Journal of Physiology, vol. 263, 1992, pp. E988-E1001.

Hellerstein et al., "Altered Fluxes Responsible for Reduced Hepatic Glucose Production and Gluconeogenesis by Exogenous Glucose in Rats", The American Journal of Physiology, vol. 272, 1997, pp. E163-E172.

Hellerstein et al., "Directly Measured Kinetics of Circulating T Lymphocytes in Normal and HIV-1-Infected Humans", Nature Medicine, vol. 5, 1999, pp. 83-89.

Hellerstein et al., "Effects of Cigarette Smoking and its Cessation on Lipid Metabolism and Energy Expenditure in Heavy Smokers", J. Clin. Invest., vol. 93, 1994, pp. 265-272.

Hellerstein et al., "Glycoconjugates as Noninvasive Probes of Intrahepatic Metabolism: Pathways of Glucose Entry into Compartmentalized Hepatic UDP-glucose Pools during Glycogen Accumulation", Proceedings of the National Academy of Sciences of the United States of America, vol. 83, No. 18, 1986, pp. 7044-7048.

Hellerstein et al., "Hepatic Gluconeogenic Fluxes and Glycogen Turnover During Fasting in Humans. A Stable Isotope Study", The Journal of Clinical Investigation, vol. 100, No. 5, Sep. 1997, pp. 1305-1319.

Hellerstein et al., "Mass Isotopomer Distribution Analysis at Eight Years: Theoretical, Analytic, and Experimental Considerations", The American Journal of Physiology, vol. 276, 1999, pp. E1146-E1170.

Hellerstein et al., "Mass Isotopomer Distribution Analysis for Measuring Fluxes Through Intracellular Metabolic Pathways and Biosynthetic Rates of Polymers", IFAC Modeling and Control in Biomedical Systems, 1994, pp. 353-359.

Hellerstein et al., "Measurement of Hepatic Ra UDP-Glucose in Vivo in Rats: Relation to Glycogen Deposition and Labeling Patterns", The American Journal of Physiology, vol. 272, 1997, pp. E155-E162.

Hellerstein et al., "Measurement of Synthesis Rates of Slow-turnover Proteins from 2H2O Incorporation into Non-essential Amino Acids (NEAA) and Application of Mass Isotopomer Distribution Analysis (MIDA)", Faseb Journal Experimental Biology, Meeting, vol. 16, 2002, p. A256 (Abstract only).

\* cited by examiner

METHOD FOR REPLACING BIOMARKERS OF PROTEIN KINETICS FROM TISSUE SAMPLES BY BIOMARKERS OF PROTEIN KINETICS FROM BODY FLUIDS AFTER ISOTOPIC LABELING IN VIVO

CROSS-REFERENCE TO RELATED APPLICATIONS

This application claims the benefit of U.S. Provisional Patent Application Ser. No. 61/801,815, filed Mar. 15, 2013, which is incorporated herein by reference in its entirety.

BACKGROUND

1. Field

The present disclosure relates generally to methods for measuring protein kinetics, and more specifically to methods for measuring the kinetics of tissue proteins using biomarkers in bodily fluids based on isotopic labeling.

2. Description of Related Art

Biopsy, the sampling of cells or tissues for investigation, plays a critical role in the diagnosis and treatment of a multitude of diseases (e.g., cancers). Often, biopsies are performed to garner information regarding specific proteins in a tissue of interest that are known to be significant in the pathogenesis of a disease. For example, collagen types I or VI, matrix proteins, and lumican (a matrix proteoglycan) are known to play roles in liver fibrosis. Traditionally, an invasive biopsy would be performed to allow for an investigation of collagen or lumican, including the kinetics of collagen or lumican, in a subject suffering from, or at risk for, liver fibrosis. Biopsies, like most invasive procedures, present an element of risk for the subject and are often costly.

Accordingly, a less-invasive, cost-effective alternative to biopsy that can provide information, particularly kinetics, about a tissue protein of interest would be useful.

BRIEF SUMMARY

Certain aspects of the present disclosure relate to a method for measuring the rate of synthesis, breakdown, transport, or other kinetic parameters of a protein in a tissue of medical interest, without requiring physical sampling of the tissue, by a measurement of the protein in a body fluid is provided. These methods take advantage of the discovery that target proteins in a tissue of medical interest may also be found in a body fluid (e.g., plasma) because they may escape or be released from the tissue of medical interest. Therefore, upon labeling a target protein with an isotope label (e.g., a radioactive or stable, non-radioactive isotope), the isotope-labeled protein may be collected, enriched, and/or isolating from the body fluid, which advantageously may be accessed in a less intrusive manner than the tissue of medical interest itself.

Accordingly, in some embodiments, the method includes selecting one or more target proteins in a tissue; administering an isotope-labeled molecule to a subject for a period of time sufficient for the isotope-labeled molecule to enter into and label the one or more target proteins to produce one or more isotope-labeled target proteins; collecting a volume of a body fluid, wherein the volume contains one or more isotope-labeled target proteins that escaped or were released from the tissue; enriching or isolating the one or more isotope-labeled target proteins from the volume; performing a mass spectrometric measurement of the isotopic content, rate of incorporation, and/or pattern or rate of change in isotopic content and/or pattern of isotope labeling of the one or more enriched or isolated isotope-labeled target proteins; and calculating at least one kinetic parameter of the one or more enriched or isolated isotope-labeled target proteins, wherein the kinetic parameter of the one or more isotope-labeled target proteins from the volume of a body fluid reflects the corresponding kinetic parameter of the one or more target proteins in the tissue; and inferring the at least one kinetic parameter of the one or more target proteins in the tissue based on the corresponding at least one kinetic parameter of the one or more target proteins in the body fluid.

DETAILED DESCRIPTION

The following description sets forth exemplary methods, parameters and the like. It should be recognized, however, that such description is not intended as a limitation on the scope of the present disclosure but is instead provided as a description of exemplary embodiments.

Described herein is a method for non-invasively measuring from a body fluid the rate of protein synthesis or protein breakdown in a tissue of medical interest as a diagnostic biomarker (e.g., protein kinetic biomarker), thereby avoiding the need for invasive sampling of the tissue of interest. Tissues of medical interest may include but are not limited to skeletal muscle, heart muscle, fibroblasts in liver or other tissues, pancreatic β-cells, or cancer tissues, and sampled body fluids may include but are not limited to blood, cerebrospinal fluid, saliva, or urine.

Figure 1:
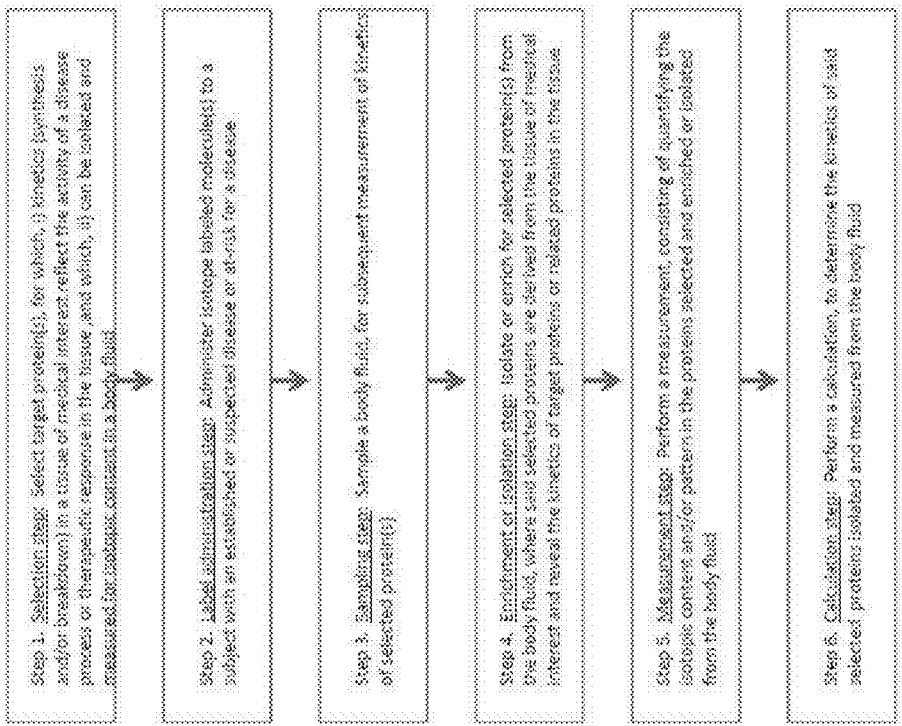
FIG. 1 depicts an exemplary overview of a "virtual biopsy" method.

FIG. 1 provides an exemplary overview of an embodiment of the virtual biopsy process. The process includes a selection step of selecting a targeted protein or proteins whose kinetics in a tissue of medical interest reflect a disease process or therapeutic response in the tissue and provide information about the disease process in the tissue. The selection can be informed through experimental measurement of kinetics of the protein(s) in the tissue or through published information about kinetics of the protein(s) in the tissue, or by a combination thereof. Step 2 is a label administration step that may include administering a stable- or radio-isotopic tracer (including but not limited to $^2H_2O$, $^{13}C_2$-leucine, $^3H$-phenylalanine, $^{13}C$-glucose, $^{13}C$-acetate, $^{15}N$-glycine, $^{15}N$-labeled spirulina) that is metabolically incorporated into newly synthesized proteins to a subject with an established or suspected disease condition in the tissue of interest, or to a subject at risk for a disease condition in the tissue of interest, for a sufficient period of time to label the target protein(s) that are undergoing synthesis in the tissue of interest. Sampling of volume of a body fluid is then performed in the subject, the body fluid including but not limited to blood, urine, sputum, or cerebrospinal fluid. An enrichment or isolation step is then performed, wherein targeted proteins that are synthesized in the tissue, that derive solely or primarily from the tissue of origin, and that then escape into an accessible body fluid, are isolated, enriched, or purified from the volume of the body fluid. The pathway of escape from the tissue of origin into the body fluid can be via secretion, exocytosis, membrane leakage, targeted vesicular fusion, attachment on exosomes, death of the cell, or any other biologic or pathologic process of escape. The protein(s) or peptides from the protein(s) are then isolated from the body fluid by methods known in the art, including but not limited to immuno-isolation, physical separation on gels or columns, liquid chromatographic separation, partial enzymatic hydrolysis followed by anti-peptide immuno-isolation, physical separation, or tandem mass spectrometry. A measurement step is then performed, which may include measuring the isotopic content and/or pattern in the target proteins by, in a preferred embodiment, use of mass spectrometry of peptides from the targeted proteins. Finally, a calculation step is carried out to determine the kinetics of the targeted proteins isolated from the body fluid. In this manner, a "virtual biopsy" of the target protein(s) from the tissue of origin will have been carried out, without requiring a physical sample from the tissue of medical interest.

In a preferred embodiment disclosed here, creatine kinase MM was targeted as a protein kinetic biomarker of skeletal muscle protein synthesis and breakdown, for use in diagnosis and drug development for sarcopenia, cachexia, muscular dystrophies, exercise training, and other medical conditions. $^2H_2O$ was administered to humans or experimental animals, and plasma creatine kinase MM was isolated from plasma by immunoprecipitation, subjected to trypsin digestion, and analyzed by LC/MS/MS (liquid chromatography-tandem mass spectrometry) to determine alterations in mass isotopomer pattern, from which the synthesis rate of creatine kinase MM in blood plasma was calculated. The synthesis rate of plasma creatine kinase MM was verified to closely reflect the synthesis rate of creatine kinase MM isolated from muscle biopsies in the same subjects, and the synthesis rates of plasma creatine kinase MM or skeletal muscle creatine kinase MM closely correlated with the synthesis rates of several other muscle proteins. In contrast, creatine kinase MB (cardiac muscle-specific) that was isolated from plasma exhibited much higher synthesis rates than creatine kinase MM, indicating tissue-specific measurement of creatine kinase synthesis from blood measurements.

In another embodiment disclosed here, the collagen fibril-associated protein lumican was targeted in plasma as a biomarker of tissue fibrogenesis (e.g., accumulation of fibroblast-derived collagen in the extracellular matrix of tissues), for use in diagnosis and drug development in fibrosis of liver, lung, heart, skin, kidney or other tissues. $^2H_2O$ was administered to humans and experimental animals and lumican-derived peptides were isolated and identified by LC/MS/MS. Alterations in mass isotopomer pattern were measured, from which the synthesis rate of lumican in blood plasma was calculated. The synthesis rate of plasma lumican was verified to closely reflect the synthesis rate of collagen Types I, III, and VI in the liver of patients with hepatitis and suspected fibrosis, in the same subjects, indicating measurement of liver fibrogenesis rate from a blood measurement.

The "virtual biopsy" method disclosed here is generalizable to many tissues and disease processes and has utility as biomarkers that can be used in drug discovery and development, or to identify disease subsets in personalized medicine, or for clinical diagnosis and management of patients.

I. GENERAL TECHNIQUES

The practice of the present disclosure will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) 3. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Cabs, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); and Mass isotopomer distribution analysis at eight years: theoretical, analytic and experimental considerations by Hellerstein and Neese (Am J Physiol 276 (Endocrinol Metab. 39) E1146-E1162, 1999). Furthermore, procedures employing commercially available assay kits and reagents will typically be used according to manufacturer-defined protocols unless otherwise noted.

U.S. Pat. No. 8,129,335, which is incorporated by reference in its entirety, provides methods and disclosures that may be useful for practice of methods described herein.

II. DEFINITIONS

Unless otherwise defined, all terms of art, notations and other scientific terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, Mass isotopomer distribution analysis at eight years: theoretical, analytic and experimental considerations by Hellerstein and Neese (Am J Physiol 276 (Endocrinol Metab. 39) E1146-E1162, 1999). As appropriate, procedures involving the use of commercially available kits and reagents are generally carried out in accordance with manufacturer defined protocols and/or parameters unless otherwise noted.

"Kinetic parameters" and "molecular flux rates" may be used interchangeably herein and may refer to the rate of synthesis, breakdown, and/or transport of a protein. "Kinetic parameters" or "molecular flux rates" also refer to a protein's input into or removal from a pool of molecules, and are therefore synonymous with the flow into and out of the pool of molecules.

"Isotopologues" refer to isotopic homologues or molecular species that have identical elemental and chemical compositions but differ in isotopic content (e.g., $CH_3NH_2$ vs. $CH_3NHD$ in the example above). Isotopologues are defined by their isotopic composition; therefore, each isotopologue has a unique exact mass but may not have a unique structure. An isotopologue usually includes of a family of isotopic isomers (isotopomers) which differ by the location of the isotopes on the molecule (e.g., $CH_3NHD$ and $CH_2DNH_2$ are the same isotopologue but are different isotopomers).

"Isotope-labeled water" includes water labeled with one or more specific heavy isotopes of either hydrogen or oxygen. Specific examples of isotope-labeled water include $^2H_2O$, $^3H_2O$, and $H_2^{18}O$.

"Protein precursor" refers to any organic or inorganic molecule or component thereof, wherein one or more atoms of which are capable of being incorporated into protein molecules in cell, tissue, organism, or other biological system, through the biochemical processes of the cell, tissue, or organism. Examples of protein precursors include, but are not limited to, amino acids, $^2H_2O$, $CO_2$, $NH_3$, and $HCO_3$.

"Isotope-labeled protein precursor" refers to a protein precursor that contains an isotope of an element that differs from the most abundant isotope of the element present in nature, cells, tissue, or organisms. The isotope label may include specific heavy isotopes of elements present in biomolecules, such as $^2H$, $^{13}C$, $^{15}N$, $^{18}O$, $^{33}S$, $^{34}$, or may contain other isotopes of elements present in biomolecules such as $^3H$, $^{14}C$, $^{35}S$, $^{125}I$, $^{131}I$. Isotope labeled protein precursors include; but are not limited to $^2H_2O$, $^{15}NH_3$, $^{13}CO_2$, $H1^{13}CO_3$, $^2H$-labeled amino acids, $^{13}C$ labeled amino acids, $^{15}N$ labeled amino acids, $^{18}O$ labeled amino acids, $^{34}S$ or $^{33}S$ labeled amino acids, $^3H_2O$, $^3H$-labeled amino acids, and $^{14}C$ labeled amino acids.

"Isotope-labeled organic metabolite precursors" refer to an organic metabolite precursor that contains an isotope of an element that differs from the most abundant isotope of the element present in nature or cells, tissues, or organisms. Isotopic labels include specific heavy isotopes of elements, present in biomolecules, such as $^2H$, $^{13}C$, $^{15}N$, $^{18}O$, $^{35}S$, $^{34}$, or may contain other isotopes of elements present in biomolecules, such as $^3H$, $^{14}C$, $^{35}S$, $^{125}I$, $^{131}I$. Isotope labeled organic metabolite precursors include but are not limited to $^2H_2O$, $^{15}NH_3$, $^{13}CO_2$, $H^{13}CO_3$, $^2H$-labeled amino acids, $^{13}C$-labeled amino acids, $^{15}N$-labeled amino acids, $^{18}O$-labeled amino acids, $^{33}S$ or $^{34}S$-labeled amino acids, $^3H_2O$, $^3H$-labeled amino acids, $^{14}C$-labeled amino acids, $^{14}CO_2$, and $H^{14}CO_2$.

"Partially purifying" refers to methods of removing one or more components of a mixture of other similar compounds. For example, "partially purifying a protein" refers to removing one or more proteins from a mixture of one or more proteins. As used herein, the term "enriching" may be used interchangeably.

"Isolating" refers to separating one compound from a mixture of compounds. For example, "isolating a protein" refers to separating one specific protein from all other proteins in a mixture of one or more proteins.

A "biological sample" encompasses any sample obtained from a cell, tissue, or organism. The definition encompasses blood and other liquid samples of biological origin, that are accessible from an organism through sampling by minimally invasive or non-invasive approaches (e.g., urine collection, blood drawing, needle aspiration, and other procedures involving minimal risk, discomfort or effort). The definition also includes samples that have been manipulated in any way after their procurement, such as by treatment with reagents, solubilization, or enrichment for certain components, such as proteins or organic metabolites. The term "biological sample" also encompasses a clinical sample such as serum, plasma, other biological fluid, or tissue samples, and also includes cells in culture, cell supenatants and cell lysates. A volume of a body fluid may be used to refer to a liquid biological sample.

"Body fluid" refers to, but is not limited to, urine, blood, interstitial fluid, edema fluid, saliva, lacrimal fluid, inflammatory exudates, synovial fluid, abscess, empyema or other infected fluid, cerebrospinal fluid, sweat, pulmonary secretions (sputum), seminal fluid, feces, bile, intestinal secretions, or other biological fluid.

"Exact mass" refers to mass calculated by summing the exact masses of all the isotopes in the formula of a molecule (e.g., 32.04847 for $CH_3NHD$).

"Nominal mass" refers to the integer mass obtained by rounding the exact mass of a molecule.

"Mass isotopomer" refers to family of isotopic isomers that is grouped on the basis of nominal mass rather than isotopic composition. A mass isotopomer may comprise molecules of different isotopic compositions, unlike an isotopologue (e.g., $CH_3NHD$, $^{13}CH_3NH_2$, $CH_3^{15}NH_2$ are part of the same mass isotopomer but are different isotopologues). In operational terms, a mass isotopomer is a family of isotopologues that are not resolved by a mass spectrometer. For quadrupole mass spectrometers, this typically means that mass isotopomers are families of isotopologues that share a nominal mass. Thus, the isotopologues $CH_3NH_2$ and $CH_3NHD$ differ in nominal mass and are distinguished as being different mass isotopomers, but the isotopologues $CH_3NHD$, $CH_2DNH_2$, $^{13}CH_3NH_2$, and $CH_3^{15}NH_2$ are all of the same nominal mass and hence are the same mass isotopomers. Each mass isotopomer is therefore typically composed of more than one isotopologue and has more than one exact mass. The distinction between isotopologues and mass isotopomers is useful in practice because all individual isotopologues are not resolved using quadrupole mass spectrometers and may not be resolved even using mass spectrometers that produce higher mass resolution, so that calculations from mass spectrometric data must be performed on the abundances of mass isotopomers rather than isotopologues. The mass isotopomer lowest in mass is represented as $M_0$; for most organic molecules, this is the species containing all $^{12}C$, $^{1}H$, $^{16}O$, $^{14}N$, etc. Other mass isotopomers are distinguished by their mass differences from $M_0$ ($M_1$, $M_2$, etc.). For a given mass isotopomer, the location or position of isotopes within the molecule is not specified and may vary (i.e., "positional isotopomers" are not distinguished).

"Mass isotopomer envelope" refers to the set of mass isotopomers associated with a molecule or ion fragment.

"Mass isotopomer pattern" refers to a histogram of the abundances of the mass isotopomers of a molecule. Traditionally, the pattern is presented as percent relative abundances where all of the abundances are normalized to that of the most abundant mass isotopomer; the most abundant isotopomer is said to be 100%. The preferred form for applications involving probability analysis, such as mass isotopomer distribution analysis (MIDA), however, is proportion or fractional abundance, where the fraction that each species contributes to the total abundance is used. The term "isotope pattern" may be used synonymously with the term "mass isotopomer pattern."

"Monoisotopic mass" refers to the exact mass of the molecular species that contains all $^{1}H$, $^{12}C$, $^{14}N$, $^{16}O$, $^{32}S$, s etc. For isotopologues composed of C, H, N, O, P, S, F, Cl, Br, and I, the isotopic composition of the isotopologue with the lowest mass is unique and unambiguous because the most abundant isotopes of these elements are also the lowest in mass. The monoisotopic mass is abbreviated as $m_0$, and the masses of other mass isotopomers are identified by their mass differences from $m_0$ ($m_1$, $m_2$, etc.).

"Isotopically perturbed" refers to the state of an element or molecule that results from the explicit incorporation of an element or molecule with a distribution of isotopes that differs from the distribution found in nature, whether a naturally less abundant isotope is present in excess (enriched) or in deficit (depleted).

"Monomer" refers to a chemical unit that combines during the synthesis of a polymer and which is present two or more times in the polymer.

"Polymer" refers to a molecule synthesized from and containing two or more repeats of a monomer.

"Protein" refers to a polymer of amino acids. As used herein, a "protein" may refer to long amino acid polymers as well as short polymers such as peptides.

III. METHODS OF THE DISCLOSURE

The present disclosure is directed to methods measuring the kinetic parameters of a protein in a tissue of medical interest, without requiring physical sampling of the tissue, by a measurement of the protein in a body fluid. The methods may include selecting one or more target proteins in a tissue; administering an isotope-labeled molecule to a subject for a period of time sufficient for the isotope-labeled molecule to enter into and label the one or more target proteins to produce one or more isotope-labeled target proteins; collecting a volume of a body fluid, where the volume contains one or more isotope-labeled target proteins that escaped or were released from the tissue; enriching or isolating the one or more isotope-labeled target proteins from the volume; performing a mass spectrometric measurement of the isotopic content, rate of incorporation, and/or pattern or rate of change in isotopic content and/or pattern of isotope labeling of the one or more enriched or isolated isotope-labeled target proteins; calculating at least one kinetic parameter of the one or more enriched or isolated isotope-labeled target proteins, where the kinetic parameter of the one or more isotope-labeled target proteins from the volume of a body fluid reflects the corresponding kinetic parameter of the one or more target proteins in the tissue; and inferring the at least one kinetic parameter of the one or more target proteins in the tissue based on the corresponding at least one kinetic parameter of the one or more target proteins in the body fluid. The relative and absolute mass isotopomer abundances of the ions within the isotopomeric envelope corresponding to each identified target protein or peptide are quantified by mass spectrometry, and the molecular flux rates of each identified target protein or peptide are calculated to determine the kinetic parameters of the target protein(s).

A. Selecting a Target Protein

Suitable target proteins may include any protein detectable in a body fluid. In some embodiments, a target protein is related to tissue collagen deposition or fibril formation. In some embodiments, a target protein may be derived from collagen-synthesizing fibroblasts. In some embodiments, target proteins may include lumican, perlecan, fibronectin, procollagen, and collagen. In some embodiments, a target protein may include any creatine kinase protein (e.g., any protein known or predicted to have the enzymatic activity of EC 2.7.3.2). A creatine kinase protein may consist of two subunits that are either brain type (B) or muscle type (M). As such, a creatine kinase protein may be a combination of subunits, including MM, MB, and BB. Different tissues are known to express different proportions of these proteins. For example, creatine kinase MM is known to be highly specific for skeletal muscle, and cardiac tissue (e.g., myocardium) is known to express a higher proportion of creatine kinase MB than other tissues. In some embodiments a target protein may include a blood protein derived from pancreatic β-cell secretory granules, e.g., insulin.

B. Administering an Isotope-Labeled Molecule

1. Labeled Precursor Molecules a. Isotope Labels

The first step in measuring molecular flux rates involves administering an isotope-labeled precursor molecule to a cell, tissue, or organism. The isotope labeled precursor molecule may be a stable isotope or radioisotope. Isotope labels that can be used include, but are not limited to, $^{2}H$, $^{13}C$, $^{15}N$, $^{18}O$, $^{3}H$, $^{14}C$, $^{35}S$, $^{32}P$, $^{125}I$, $^{131}I$, or other isotopes of elements present in organic systems. In one embodiment, the isotope label is $^{2}H$.

b. Precursor Molecules

The precursor molecule may be any molecule having an isotope label that is incorporated into a protein or organic metabolite. Isotope labels may be used to modify all precursor molecules disclosed herein to form isotope-labeled precursor molecules.

The entire precursor molecule may be incorporated into one or more proteins and/or organic metabolites. Alternatively, a portion of the precursor molecule may be incorporated into one or more proteins and/or organic metabolite.

Precursor molecules may include, but not limited to, $CO_2$, $NH_3$, glucose, lactate, $^{2}H_2O$, acetate, and fatty acids.

i. Protein Precursors

A protein precursor molecule may be any protein precursor molecule known in the art. These precursor molecules may be $CO_2$, $NH_3$, glucose, lactate, $H_2O$, acetate, and fatty acids.

Precursor molecules of proteins may also include one or more amino acids. The precursor may be any amino acid. The precursor molecule may be a singly or multiply deuterated amino acid. For example, the precursor molecule may be one or more of $^{13}$C-lysine, $^{15}$N-histidine, $^{13}$C-serine, $^{13}$C-glycine, $^{2}$H-leucine, $^{15}$N-glycine, $^{13}$C-leucine, $^{2}$H$_5$-histidine, and any deuterated amino acid. Labeled amino acids may be administered, for example, undiluted or diluted with non-labeled amino acids. All isotope labeled precursors may be purchased commercially, for example, from Cambridge Isotope Labs (Andover, Mass.).

Protein precursor molecules may also include any precursor for post-translational or pre-translationally modified amino acids. These precursors include but are not limited to precursors of methylation such as glycine, serine or $H_2O$; precursors of hydroxylation, such as H.sub.2O or O.sub.2; precursors of phosphorylation, such as phosphate, $H_2O$ or $O_2$; precursors of prenylation, such as fatty acids, acetate, $H_2O$, ethanol, ketone bodies, glucose, or fructose; precursors of carboxylation, such as $CO_2$, $O_2$, $H_2O$, or glucose; precursors of acetylation, such as acetate, ethanol, glucose, fructose, lactate, alanine, $H_2O$, $CO_2$, or $O_2$; and other post-translational modifications known in the art.

The degree of labeling present in free amino acids may be determined experimentally, or may be assumed based on the number of labeling sites in an amino acid. For example, when using hydrogen isotopes as a label, the labeling present in C—H bonds of free amino acid or, more specifically, in tRNA-amino acids, during exposure to $^{2}H_2O$ in body water may be identified. The total number of C—H bonds in each non-essential amino acid is known—e.g., 4 in alanine, 2 in glycine, etc.

The precursor molecule for proteins may be water. The hydrogen atoms on C—H bonds are the hydrogen atoms on amino acids that are useful for measuring protein synthesis from $^{2}H_2O$ since the O—H and N—H bonds of proteins are labile in aqueous solution. As such, the exchange of $^{2}$H-label from $^{2}H_2O$ into O—H or N—H bonds occurs without the synthesis of proteins from free amino acids as described above. C—H bonds undergo incorporation from $H_2O$ into free amino acids during specific enzyme-catalyzed intermediary metabolic reactions. The presence of $^{2}$H-label in C—H bonds of protein-bound amino acids after $^{2}H_2O$ administration therefore means that the protein was assembled from amino acids that were in the free form during the period of $^{2}H_2O$ exposure—i.e., that the protein is newly synthesized. Analytically, the amino add derivative used must contain all the C—H bonds but must remove all potentially contaminating N—H and O—H bonds.

Hydrogen atoms from body water may be incorporated into free amino acids. $^{2}$H or $^{3}$H from labeled water can enter into free amino adds in the cell through the reactions of intermediary metabolism, but .sup.2H or .sup.3H cannot enter into amino acids that are present in peptide bonds or that are bound to transfer RNA. Free essential amino acids may incorporate a single hydrogen atom from body water into the .alpha.-carbon C—H bond, through rapidly reversible transamination reactions. Free non-essential amino adds contain a larger number of metabolically exchangeable C—H bonds, of course, and are therefore expected to exhibit higher isotopic enrichment values per molecule from $^{2}H_2O$ in newly synthesized proteins.

One of skill in the art will recognize that labeled hydrogen atoms from body water may be incorporated into other amino acids via other biochemical pathways. For example, it is known in the art that hydrogen atoms from water may be incorporated into glutamate via synthesis of the precursor α-ketoglutrate in the citric acid cycle. Glutamate, in turn, is known to be the biochemical precursor for glutamine, proline, and arginine. By way of another example, hydrogen atoms from body water may be incorporated into post-translationally modified amino acids, such as the methyl group in 3-methyl-histine, the hydroxyl group in hydroxyproline or hydroxylysine, and others. Other amino adds synthesis pathways are known to those of skill in the art.

Oxygen atoms ($H_2^{18}O$) may also be incorporated into amino acids through enzyme-catalyzed reactions. For example, oxygen exchange into the carboxylic acid moiety of amino acids may occur during enzyme catalyzed reactions. Incorporation of labeled oxygen into amino acids is known to one of skill in the art. Oxygen atoms may also be incorporated into amino acids from $^{18}O_2$ through enzyme catalyzed reactions (including hydroxyproline, hydroxylysine or other post-translationally modified amino acids).

Hydrogen and oxygen labels from labeled water may also be incorporated into amino acids through post-translational modifications. In one embodiment, the post-translational modification may already include labeled hydrogen or oxygen through biosynthetic pathways prior to post-translational modification. In another embodiment, the post-translational modification may incorporate labeled hydrogen, oxygen, carbon, or nitrogen from metabolic derivatives involved in the free exchange labeled hydrogens from body water, either before or after post-translational modification step (e.g. methylation, hydroxylation, phosphorylation, prenylation, sulfation, carboxylation, acetylation or other known post-translational modifications).

Protein precursors for that are suitable for administration into a subject include, but are not limited to $H_2O$, $CO_2$, $NH_3$ and $HCO_3$, in addition to the standard amino acids found in proteins.

ii. Modes of Administering Precursors of Proteins

Modes of administering the one or more isotope-labeled precursors may vary, depending upon the absorptive properties of the isotope-labeled precursor and the specific biosynthetic pool into which each compound is targeted. Precursors may be administered to organisms, plants and animals including humans directly for in vivo analysis. In addition, precursors may be administered in vitro to living cells. Specific types of living cells include hepatocytes, adipocytes, myocytes, fibroblasts, neurons, pancreatic β-cells, intestinal epithelial cells, leukocytes, lymphocytes, erythrocytes, microbial cells and any other cell-type that can be maintained alive and functional in vitro.

Generally, an appropriate mode of administration is one that produces a steady state level of precursor within the biosynthetic pool and/or in a reservoir supplying such a pool for at least a transient period of time. Intravenous or oral routes of administration are commonly used to administer such precursors to organisms, including humans. Other routes of administration, such as subcutaneous or intra-muscular administration, optionally when used in conjunction with slow release precursor compositions, are also appropriate. Compositions for injection are generally prepared in sterile pharmaceutical excipients. Modes of administration may comprise continuous administration or discontinuous administration (e.g., a pulse chase).

B. Collecting a Volume of a Body Fluid Containing Isotope-Labeled Proteins

In practicing the method of the invention, in one aspect, proteins and organic metabolites are obtained from a cell, tissue, or organism according to the methods known in the art. The methods may be specific to the proteins or organic metabolites of interest. Proteins and organic metabolites of interest may be isolated from a biological sample.

A plurality of proteins or a plurality of organic metabolites may be acquired from the cell, tissue, or organism. The one or more biological samples may be obtained, for example, by blood draw, urine collection, biopsy, or other methods known in the art. The one or more biological sample may be a volume of one or more biological fluids. The protein or organic metabolite may also be obtained from specific organs or tissues, such as muscle, liver, adrenal tissue, prostate tissue, endometrial tissue, blood, skin, and breast tissue. Proteins or organic metabolites may be obtained from a specific group of cells, such as tumor cells or fibroblast cells.

The frequency of biological sampling can vary depending on different factors. Such factors include, but are not limited to, the nature of the proteins or organic metabolites, ease and safety of sampling, synthesis and breakdown/removal rates of the proteins or organic metabolites from which it was derived, and the half-life of a therapeutic agent or biological agent.

The proteins or organic metabolites may also be purified partially, or optionally, isolated, by conventional purification methods including high pressure liquid chromatography (HPLC), fast performance liquid chromatography (FPLC), chemical extraction, thin layer chromatography, gas chromatography, gel electrophoresis, and/or other separation methods known to those skilled in the art.

In another embodiment, the proteins or organic metabolites may be hydrolyzed or otherwise degraded to form smaller molecules. Hydrolysis methods include any method known in the art, including, but not limited to, chemical hydrolysis (such as acid hydrolysis) and biochemical hydrolysis (such as peptidase degradation). Hydrolysis or degradation may be conducted either before or after purification and/or isolation of the proteins or organic metabolites. The proteins or organic metabolites also may be partially purified, or optionally, isolated, by conventional purification methods including high performance liquid chromatography (HPLC), fast performance liquid chromatography (FPLC), gas chromatography, gel electrophoresis, and/or any other methods of separating chemical and/or biochemical compounds known to those skilled in the art.

C. Enriching or Isolating an Isotope-Labeled Protein

In some embodiments, an isotope-labeled target protein is enriched or isolated from a volume of body fluid. Proteins or organic metabolites may be partially purified, enriched, or isolated, from a biological sample (e.g., a volume of body fluid) using standard biochemical methods known in the art. For example, suitable methods of enriching or isolating a protein may include, but are not limited to, immunoprecipitation, chromatography (e.g., by size exclusion, hydrophobic interaction, affinity, metal binding, immunoaffinity, or HPLC), centrifugation through a density gradient, etc. Suitable methods for enrichment and isolation may depend upon, for example, protein abundance, biochemical properties of the protein, the type of sample (e.g., body fluid), and the relative degree of enrichment or purity required.

D. Performing a Mass Spectrometric Measurement

Isotopic enrichment in proteins and organic metabolites can be determined by various methods such as mass spectrometry, including but not limited to liquid chromatography-tandem mass spectrometry (LC/MS/MS), gas chromatography-mass spectrometry (GC-MS), isotope-ratio mass spectrometry, GC-isotope ratio-combustion-MS, GC-isotope ratio-pyrrolysis-MS, liquid chromatography-MS, electro-spray ionization-MS, matrix assisted laser desorption-time of flight-MS, Fourier-transform-ion-cyclotron-resonance-MS, and cycloidal-MS.

Mass spectrometers convert molecules such as proteins and organic metabolites into rapidly moving gaseous ions and separate them on the basis of their mass-to-charge ratios. The distributions of isotopes or isotopologues of ions, or ion fragments, may thus be used to measure the isotopic enrichment in a plurality of proteins or organic metabolites.

Generally, mass spectrometers include an ionization means and a mass analyzer. A number of different types of mass analyzers are known in the art. These include, but are not limited to, magnetic sector analyzers, electrospray ionization, quadrupoles, ion traps, time of flight mass analyzers, and Fourier transform analyzers.

Mass spectrometers may also include a number of different ionization methods. These include, but are not limited to, gas phase ionization sources such as electron impact, chemical ionization, and field ionization, as well as desorption sources, such as field desorption, fast atom bombardment, matrix assisted laser desorption/ionization, and surface enhanced laser desorption/ionization.

In addition, two or more mass analyzers may be coupled (MS/MS) first to separate precursor ions, then to separate and measure gas phase fragment ions. These instruments generate an initial series of ionic fragments of a protein, and then generate secondary fragments of the initial ions. The resulting overlapping sequences allows complete sequencing of the protein, by piecing together overlaying "pieces of the puzzle" based on a single mass spectrometric analysis within a few minutes (plus computer analysis time).

The MS/MS peptide fragmentation patterns and peptide exact molecular mass determinations generated by protein mass spectrometry provide unique information regarding the amino acid sequence of proteins and find use in the present invention. An unknown protein can be sequenced and identified in minutes, by a single mass spectrometric analytic run. The library of peptide sequences and protein fragmentation patterns that is now available provides the opportunity to identify components of complex proteome mixtures with near certainty.

Different ionization methods are also known in the art. One key advance has been the development of techniques for ionization of large, non-volatile macromolecules including proteins and polynucleotides. Techniques of this type have included electrospray ionization (ESI) and matrix assisted laser desorption (MALDI). These have allowed MS to be applied in combination with powerful sample separation introduction techniques, such as liquid chromatography and capillary zone electrophoresis.

In addition, mass spectrometers may be coupled to separation means such as gas chromatography (GC) and high performance liquid chromatography (HPLC). In gas-chromatography mass-spectrometry (GC/MS), capillary columns from a gas chromatograph are coupled directly to the mass spectrometer, optionally using a jet separator. In such an application, the gas chromatography (GC) column separates sample components from the sample gas mixture and the separated components are ionized and chemically analyzed in the mass spectrometer.

When GC/MS (or other mass spectrometric modalities that analyze ions of proteins and organic metabolites, rather than small inorganic gases) is used to measure mass isotopomer abundances of organic molecules, hydrogen-labeled isotope incorporation from isotope-labeled water is amplified 3 to 7-fold, depending on the number of hydrogen atoms incorporated into the organic molecule from isotope-labeled water in vivo.

In general, in order to determine a baseline mass isotopomer frequency distribution for the protein, such a sample is taken before infusion of an isotopically labeled precursor. Such a measurement is one means of establishing in the cell, tissue or organism, the naturally occurring frequency of mass isotopomers of the protein. When a cell, tissue or organism is part of a population of subjects having similar environmental histories, a population isotopomer frequency distribution may be used for such a background measurement. Additionally, such a baseline isotopomer frequency distribution may be estimated, using known average natural abundances of isotopes. For example, in nature, the natural abundance of .sup.13C present in organic carbon in 1.11%. Methods of determining such isotopomer frequency distributions are discussed below. Typically, samples of the protein are taken prior to and following administration of an isotopically labeled precursor to the subject and analyzed for isotopomer frequency as described below. Similar considerations apply to the isolation of organic molecules for Dynamic Organeomics.

Thus, a single analysis of even an enormously complex mixture of proteins (that has been subjected to proteolytic cleavage or analyzed directly) can uniquely identify peptides representing thousands of expressed proteins.

Proteins may also be detected using protein chips. Several commercial "protein chip" equivalents are now marketed, using mass spectrometry (e.g. Ciphergen Biosystems). The efficiency of peptide sequence determination by mass analysis, combined with powerful ion fragmentation technology (MS/MS instruments) and/or peptide generating biochemical methods (e.g. proteolysis), improvements in sample introduction methods (HPLC, surface desorption, etc.), improved capacity for ionization of even the largest macromolecules (ESI, MALDI/SELDI) and rapid computerized handling of large data sets and comparison to peptide/protein reference libraries, have made mass spectrometry a general and powerful tool for automated, large-scale, high-throughput static proteomics.

Measuring Relative and Absolute Mass Isotopomer Abundances

Measured mass spectral peak heights, or alternatively, the areas under the peaks, may be expressed as ratios toward the parent (zero mass isotope) isotopomer. It is appreciated that any calculation means which provides relative and absolute values for the abundances of isotopomers in a sample may be used in describing such data, for the purposes of the invention.

Calculating Labeled: Unlabeled Proportion of Proteins

The proportion of labeled and unlabeled proteins is then calculated. The practitioner first determines measured excess molar ratios for isolated isotopomer species of a molecule. The practitioner then compares measured internal pattern of excess ratios to the theoretical patterns. Such theoretical patterns can be calculated using the binomial or multinomial distribution relationships as described in U.S. Pat. Nos. 5,338,686; 5,910,403; and 6,010,846 which are hereby incorporated by reference in their entirety. The calculations may include Mass Isotopomer Distribution Analysis (MIDA). Variations of Mass Isotopomer Distribution Analysis (MIDA) combinatorial algorithm are discussed in a number of different sources known to one skilled in the art. The method is further discussed by Hellerstein and Neese (1999), as well as Chinkes, et al. (1996), and Kelleher and Masterson (1992), and U.S. patent application Ser. No. 10/279,399, all of which are hereby incorporated by reference in their entirety. In addition to the above-cited references, calculation software implementing the method is publicly available from Professor Marc Hellerstein, University of California, Berkeley.

The comparison of excess molar ratios to the theoretical patterns can be carried out using a table generated for a protein of interest, or graphically, using determined relationships. From these comparisons, a value, such as the value p, which describes the probability of mass isotopic enrichment of a subunit in a precursor subunit pool, is determined. This enrichment is then used to determine a value, such as the value A.sub.X*, which describes the enrichment of newly synthesized proteins for each mass isotopomer, to reveal the isotopomer excess ratio which would be expected to be present, if all isotopomers were newly synthesized.

Fractional abundances are then calculated. Fractional abundances of individual isotopes (for elements) or mass isotopomers (for molecules) are the fraction of the total abundance represented by that particular isotope or mass isotopomer. This is distinguished from relative abundance, wherein the most abundant species is given the value 100 and all other species are normalized relative to 100 and expressed as percent relative abundance. For a mass isotopomer $M_x$, Fractional abundance of Mx=Ax=Abundance Mxi=0 n Abundance Mi, $$\text{Fractional abundance of } M_x = A_x = \frac{\text{Abundance } M_x}{\sum_{i=0}^{n} \text{Abundance } M_i},$$

where 0 to n is the range of nominal masses relative to the lowest mass ($M_0$) mass isotopomer in which abundances occur.

$$\Delta \text{Fractional abundance(enrichment or depletion)} =$$

$$(A_x)_e - (A_x)_b = \left( \frac{\text{Abundance } M_x}{\sum_{i=0}^{n} \text{Abundance } M_i} \right)_e - \left( \frac{\text{Abundance } M_x}{\sum_{i=0}^{n} \text{Abundance } M_i} \right)_b,$$

where subscript e refers to enriched and b refers to baseline or natural abundance.

In order to determine the fraction of polymers that were actually newly synthesized during a period of precursor administration, the measured excess molar ratio ($EM_x$) is compared to the calculated enrichment value, $A_x^*$, which describes the enrichment of newly synthesized biopolymers for each mass isotopomer, to reveal the isotopomer excess ratio which would be expected to be present if all isotopomers were newly synthesized.

F. Calculating Kinetic Parameters

One skilled in the art may establish that a kinetic parameter of the one or more isotope-labeled target proteins from the volume of a body fluid reflects the corresponding kinetic parameter of the one or more target proteins in the tissue by any means known in the art, including, e.g., independently comparing measurements of the kinetic parameter of the one or more target proteins in individual subjects.

The method of determining rate of synthesis includes calculating the proportion of mass isotopically labeled subunit present in the protein precursor pool, and using this proportion to calculate an expected frequency of a protein containing at least one mass isotopically labeled subunit. This expected frequency is then compared to the actual, experimentally determined protein isotopomer frequency. From these values, the proportion of protein which is synthesized from added isotopically labeled precursors during a selected incorporation period can be determined. Thus, the rate of synthesis during such a time period is also determined.

A precursor-product relationship is then applied. For the continuous labeling method, the isotopic enrichment is compared to asymptotic (i.e., maximal possible) enrichment and kinetic parameters (e.g., synthesis rates) are calculated from precursor-product equations. The fractional synthesis rate ($k_s$) may be determined by applying the continuous labeling, precursor-product formula:

$$k_s[-\ln(1-f)/t]$$

where f=fractional synthesis=product enrichment/asymptotic precursor/enrichment and t=time of label administration of contacting in the system studied.

For the discontinuous labeling method, the rate of decline in isotope enrichment is calculated and the kinetic parameters of proteins are calculated from exponential decay equations. In practicing the method, biopolymers are enriched in mass isotopomers, preferably containing multiple mass isotopically labeled precursors. These higher mass isotopomers of the proteins, e.g., proteins containing 3 or 4 mass isotopically labeled precursors, are formed in negligible amounts in the absence of exogenous precursor, due to the relatively low abundance of natural mass isotopically labeled precursor, but are formed in significant amounts during the period of protein precursor incorporation. The proteins taken from the cell, tissue, or organism at the sequential time points are analyzed by mass spectrometry, to determine the relative frequencies of a high mass protein isotopomer. Since the high mass isotopomer is synthesized almost exclusively before the first time point, its decay between the two time points provides a direct measure of the rate of decay of the protein.

Preferably, the first time point is at least 2-3 hours after administration of precursor has ceased, depending on mode of administration, to ensure that the proportion of mass isotopically labeled subunit has decayed substantially from its highest level following precursor administration. In one embodiment, the following time points are typically 1-4 hours after the first time point, but this timing will depend upon the replacement rate of the biopolymer pool.

The rate of decay of the protein is determined from the decay curve for the three-isotope protein. In the present case, where the decay curve is defined by several time points, the decay kinetics can be determined by fitting the curve to an exponential decay curve, and from this, determining a decay constant.

Breakdown rate constants ($k_d$) may be calculated based on an exponential or other kinetic decay curve:

$$k_d[-\ln f]/t.$$

While the invention has been described with respect to specific mass isotopes and proteins, it will be appreciated how the method can be used to determine subunit pool composition, and rates of synthesis and decay for substantially any biopolymer which is formed from two or more identical subunits which can be mass isotopically labeled. Similar considerations apply for organic metabolites.

G. Inferring a Kinetic Parameter of a Protein in a Tissue

A kinetic parameter of an isotope-labeled target protein is calculated based upon measurements of the target protein enriched or isolated from a body fluid. In some embodiments, this kinetic parameter is then used to infer the corresponding kinetic parameter of the target protein in a tissue of medical interest. The kinetic parameters of the target protein in a tissue vs. body fluid may be related (i.e., the kinetic parameter of the target protein in the body fluid reflects the corresponding kinetic parameter in the tissue), but they are not required to be equivalent. The kinetic parameters in a tissue vs. in body fluid may be measured and compared by any means known in the art. The kinetic parameter of a protein in a tissue vs. that in a body fluid may be mathematically related by a known or unknown rate of protein escape or release from the tissue. Various means for determining a rate of protein escape or release from a tissue are known in the art.

Utility

Metabolic turnover kinetics of a protein of interest in a tissue of origin may be used as a diagnostic test, for the diagnosis, management or treatment selection of a human patient. By way of example, the measurement of skeletal muscle creatine kinase-MM (the terms "creatine-kinase M-type" and "CK-M" are used interchangeably herein), myoglobin, or troponin synthesis and/or breakdown rates from a body fluid can be used in the diagnosis, management or treatment selection of a patient with sarcopenia, cachexia, malnutrition, frailty, mobility disability, rehabilitation, muscular dystrophy or other disorder of skeletal muscle mass or function. The measurement of cardiac muscle creatine kinase-MB synthesis and/or breakdown rates from a body fluid in the diagnosis, management or treatment selection of a patient with heart failure, heart transplant, hypertension ischemic heart disease or other disorder of cardiac muscle mass or function. By way of another example, the rate of liver fibrogenesis can be determined from a blood measurement of lumican synthesis, for use in medical monitoring of patients with hepatitis C or B, alcoholic liver fibrosis, fatty liver disease or other fibrogenic disorders.

Example 1

Virtual Biopsy of Liver Fibrogenesis Through Measurements of Plasma Lumican from Blood Samples This example demonstrates the use of a virtual biopsy to assess liver fibrogenesis by determining liver collagen synthesis rate through a body fluid biomarker. This example further illustrates an approach to discovering a virtual biopsy body fluid biomarker of tissue protein synthesis (and a corresponding rate thereof) when the biomarker in a body fluid is not identified in advance.

Tissue Collection

A total of 11 subjects were recruited at UCSF Liver Center who were imminently undergoing diagnostic biopsy. Subjects drank heavy water, a nonradioactive, stable isotopic tracer for 14 to 56 days in an outpatient setting for the period between referral and surgical biopsy date. Blood, urine, and an 18 gauge liver biopsy were collected. 50% of the biopsy material was used to generate histological tissue slides for pathological diagnosis of disease and fibrotic intensity. The remaining tissue was used for kinetic analysis as described below. Subjects had a range of diagnoses [Hep C Virus (HCV), Autoimmune Hepatitis (AIH), Hepatocellular carcinoma (HCC)] and a range of fibrotic scores (on a scale of 0-4). The study was approved by the Committee on Human Research at UCSF. All participants gave written informed consent, and Declaration of Helsinki protocols were followed.

Liver Tissue LCMS Prep

Liver biopsy tissue from 6 patients was weighed (3-13 mg) and subsequently homogenized with a Fast Prep-24™ (MP Biomedical) bead mill in pure, deionized water. Homogenized tissue was then subjected to acetone precipitation to purify total tissue protein. 9× volumes cold acetone was mixed with homogenate and incubated at −20° C. for 20 min followed by centrifugation at 1000×g for 5 min at 4 C. Pellets were resuspended in H2O and total protein quantification performed via BCA Protein Assay Kit (Thermo, Rockford Ill.). 80 µg of liver protein from each patient was isolated and denatured using ProteasMax™ surfactant (0.1%; Promega, Madison Wis.) and urea (4M) in 25 mM ammonium bicarbonate (pH=8). The solution was reduced with TCEP (5 mM) for 20 minutes at RT with mixing, followed by incubation with iodoacetamide (10 mM) in the dark for 20 minutes to chemically modify reduced cysteines. Liver proteins were then digested with trypsin (Promega, Madison Wis.) at 37° C. overnight. The following day formic acid was added to a total volume of 5%, and peptides were concentrated and desalted prior to LC-MS/MS using a C18 spec tip (Varian, Palo Alto Calif.).

Plasma LCMS Prep

Plasma from 8 patients (10 μL) was depleted of high abundance proteins using a multi-affinity spin cartridge (Hu14, Agilent, Santa Clara, Calif.) according to the manufacturer's recommendations. Remaining protein components were quantified using a BCA Protein Assay Kit (Thermo, Rockford Ill.), and 50 μg of protein was isolated from each patient for trypsin digestion. Plasma proteins samples were denatured using ProteasMax™ surfactant (0.1%; Promega, Madison Wis.) and urea (4M) in 25 mM ammonium bicarbonate (pH=8). The solution was reduced with TCEP (5 mM) for 20 minutes at RT with mixing, followed by incubation with Iodoacetamide (10 mM) in the dark for 20 minutes to chemically modify reduced cysteines. Plasma protein was then digested with trypsin (Promega, Madison Wis.) at 37° C. overnight. The following day formic acid was added to a total volume of 5%, and peptides were concentrated and desalted prior to LC-MS/MS using a C18 spec tip (Varian, Palo Alto Calif.).

Measurement of $^2$H Enrichment in Body Water

Aliquots of plasma were diluted 1:100, and placed into the caps of inverted sealed screw-capped vials for overnight distillation at 80° C. Body water $^2$H$_2$O enrichments were determined by direct measurement of deuterium mole percent excess (MPE) in water distilled from the blood plasma. MPE was measured against a $^2$H$_2$O standard curve using laser water isotope analyzer (LGR, Los Gatos Calif.) according to the published method (G. Lis, et al., Anal. Chem. 80 (2008) 287-293).

LCMS Data Acquisition and Isotopomer Extraction

Isotopic distributions of peptides were measured using an Agilent 6550 QToF with HPLC Chip-Cube Polaris Chip (Agilent, Santa Clara Calif.). Each sample was injected two times per analysis. During the first injection MSMS fragmentation spectra were collected for peptide identification. During the second injection no MSMS fragmentations were performed and a longer dwell time (1 spectrum per second) was used in the full scan acquisition. MSMS fragmentation data was analyzed using the Agilent software package Spectrum Mill and protein identifications were based on the Uniprot/Swissprot database where species=human, trypsin digest, and carbamidomethylation of cysteine were used as restrictions on the search. Pyroglutamate, oxidized methionine, and hydroxyproline were allowed as additional modifications. Isotopomer patterns were extracted from the MS scan data using the MassHunter software package from Agilent. The peptide list with calculated neutral mass, elemental formula, and retention time was used to filter the observed isotope clusters. A visual basic application was constructed to calculate peptide elemental composition from lists of peptide sequences and calculate isotopomer patterns over a range of precursor body $^2$H$_2$O enrichments (p) for the number (n) of C—H positions actively incorporating H/D from body water. Theoretical peptide values for n were determined as previously described (J. C. Price et al., Anal. Biochem. 420 (2012) 73-83). Briefly, tryptic peptides exhibit a value of n that is the sum of the individual values of ($n_{AA}$) the amino acids that make up the peptide. Subsequent data handling was performed using Microsoft Excel.

Calculation of Protein Fractional Synthesis (f) and Turnover Rate (k).

While mass spectrometry can quantify a shift to higher masses in a peptide with 2H-labeling, kinetic interpretation of the replacement rate of pre-existing protein molecules by newly synthesized ones requires understanding of the mass isotope pattern of newly-synthesized species as compared to unlabeled species. The mass isotopomer pattern of proteins synthesized in the presence of a stable-isotopically perturbed precursor pool can be calculated by combinatorial analysis (M. K. Hellerstein and R. A. Neese, Am. J. Physiol. 276 (1999) E1146-E1170). Fractional synthesis (f) is defined as the proportion of newly synthesized proteins in a population, expressed as a fraction of the total pool. We based our calculations off on the absolute value for change in intensity of the normalized monoisotopic peak (|EM0|). In principle, the shift in intensity of any isotopic peak in the envelope should reveal the same f. In practice, we find that the signal to noise is most favorable for |EM0|, because of the larger change in fractional abundance for this isotopomer (EM0 decreases while labeled species distribute among EM1-EM4). We normalized the fractional synthesis measurements for each subject to a time-independent turnover rate, k, using the equation: k=ln(1−f)/t, where t is the duration of exposure to heavy water prior to biopsy.

Criteria for Peptides Used in Calculation of Protein Turnover Rates

Peptides which met our criteria for inclusion had signal intensity >30,000 counts. Protein turnover rates were calculated as the mean of the peptide population that passed these criteria for each protein. A minimum of 2 peptides were required to determine a protein turnover rate for each sample.

Correlation of Collagen and Lumican Kinetics with Disease

Protein turnover rates (k) from liver (n=6) and plasma (n=8) sample proteins were correlated with one another, as well as with patient histological fibrotic score (0-4). Regression analysis was performed to determine statistically significant relationships (p<0.05) (e.g. liver type-1 collagen and plasma lumican vs. fibrotic score).

Results

Figure 2:
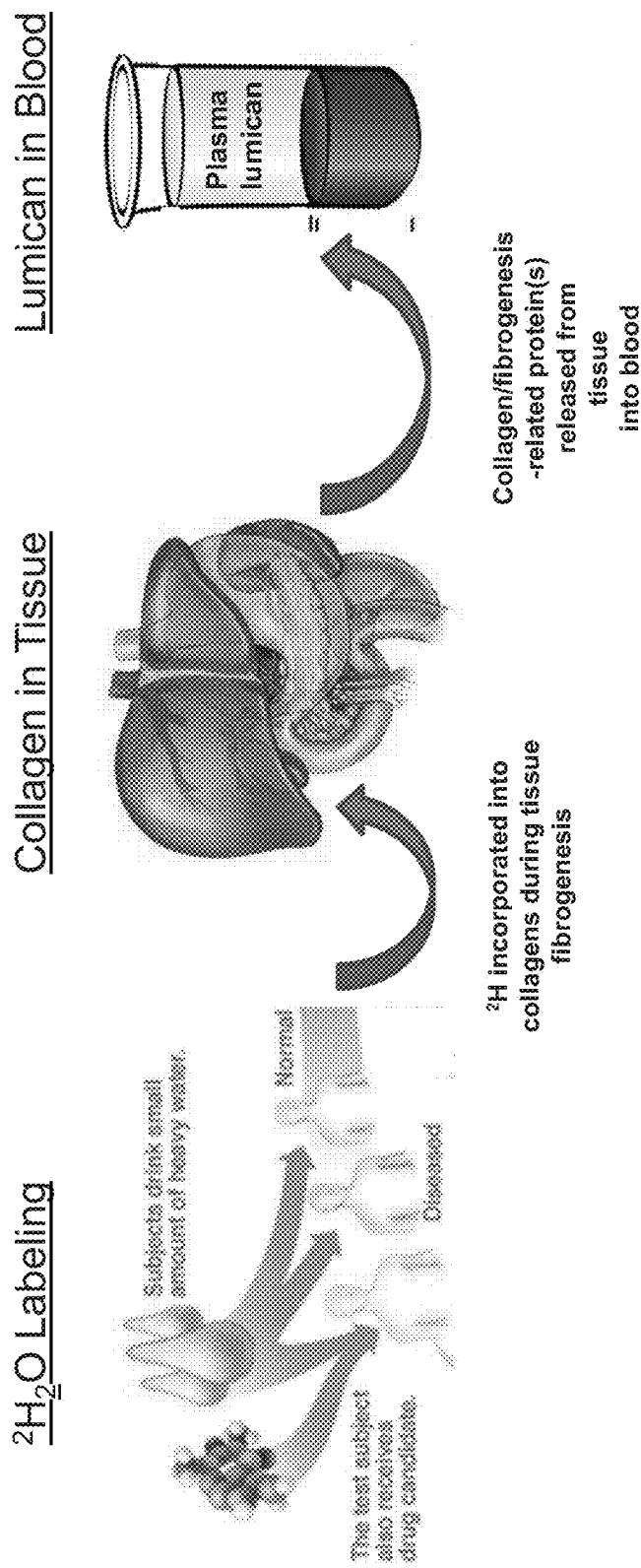
FIG. 2 illustrates an application of the "virtual biopsy" method to assess tissue fibrogenesis from measurements of isotope-labeled blood proteins.

As illustrated in FIG. 2, $^2$H$_2$O was administered to humans and became incorporated into collagens and fibrogenesis-/collagen-related proteins during tissue fibrogenesis. Blood and urine were screened for then proteins whose synthesis rate correlated with liver collagen synthesis rate in order to identify potential body fluid diagnostic biomarkers of liver fibrosis. Protein turnover rates from liver and plasma sample proteins were correlated with each other, as well as with patient histological fibrotic score, as described above. Regression analysis was performed to determine statistically significant relationships as described above.

Figure 3:
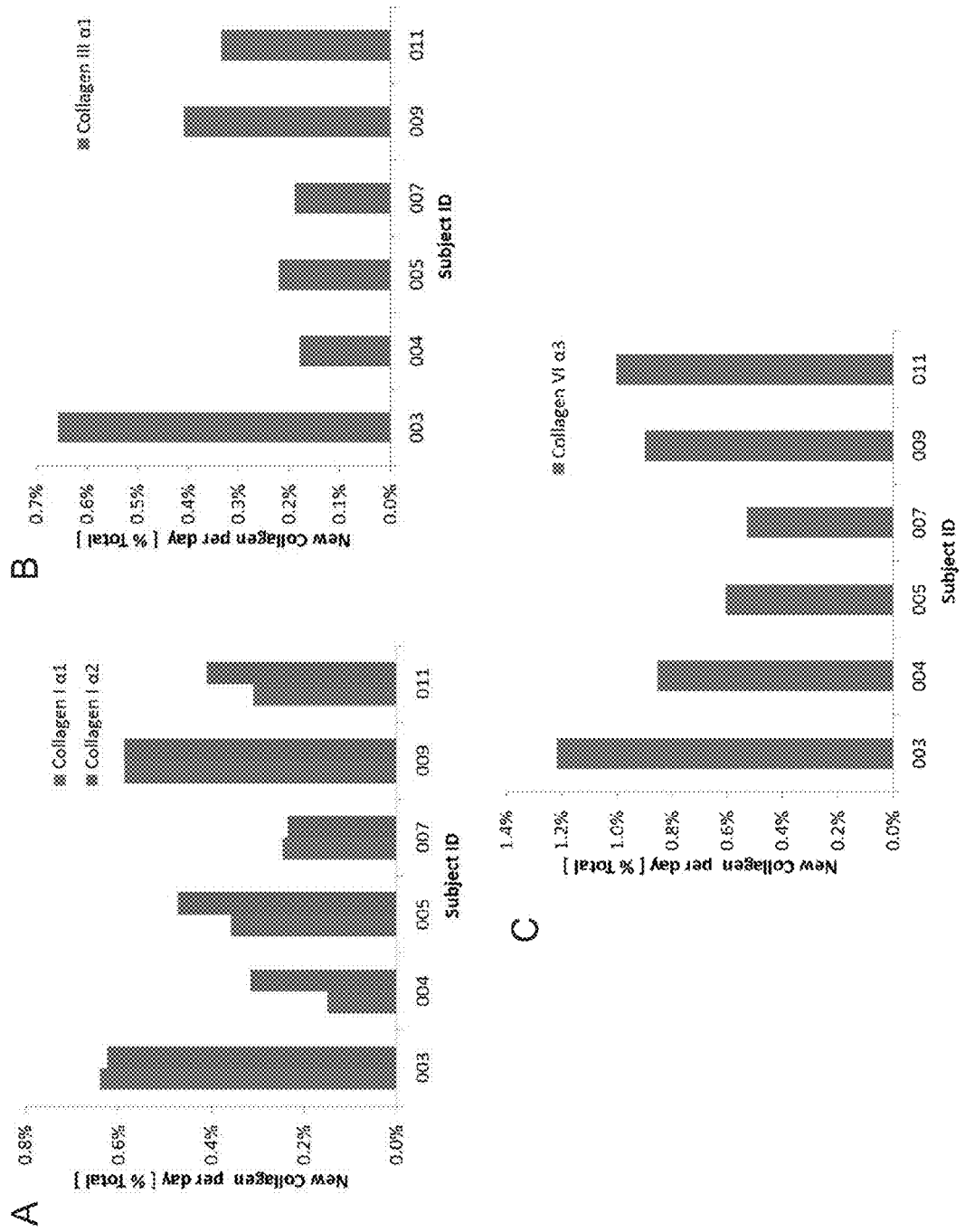
FIG. 3 shows the variation in collagen synthesis rates between individuals. Synthesis rates derived from individual subjects are provided for Collagen I α1 and α2 (A), Collagen III α1 (B), and Collagen VI α3 (C) are shown. Synthesis rates are expressed as the percentage of new collagen synthesized as a fraction of total collagen per day.
Figure 4:
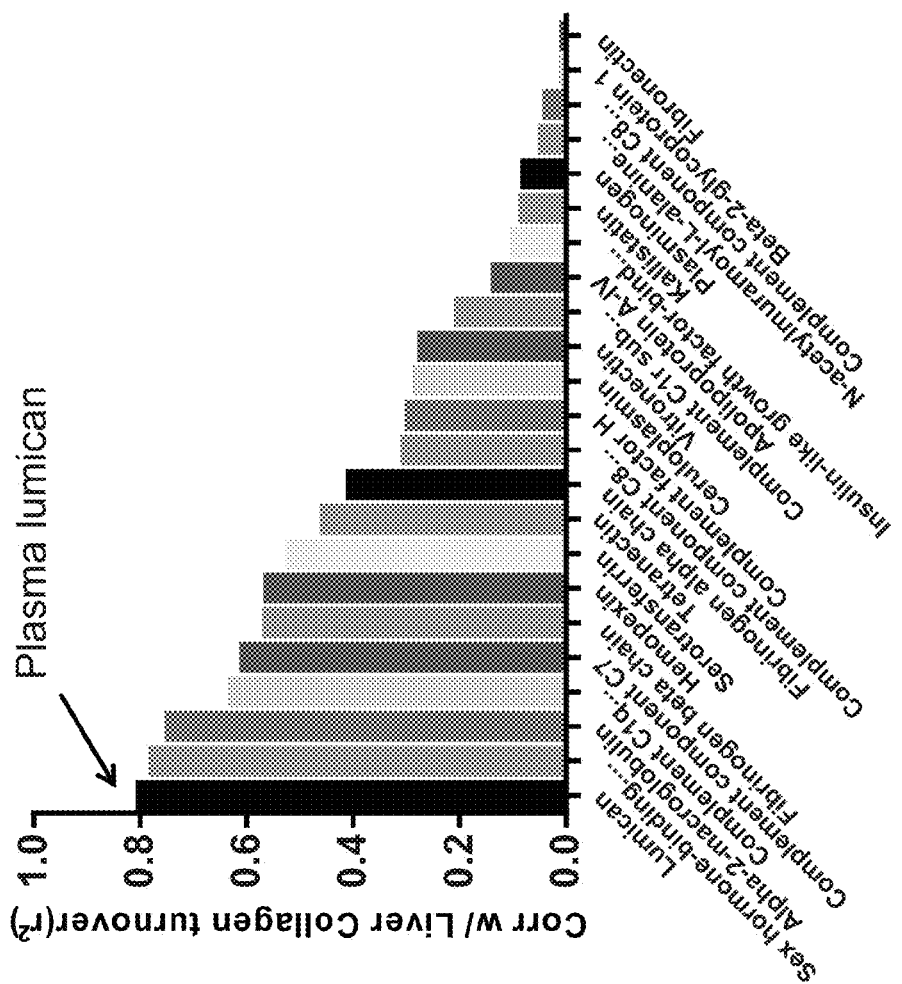
FIG. 4 shows the correlation ($r^2$ value) between different plasma proteins and liver collagen turnover. Plasma lumican demonstrates the highest correlation (labeled).
Figure 5:
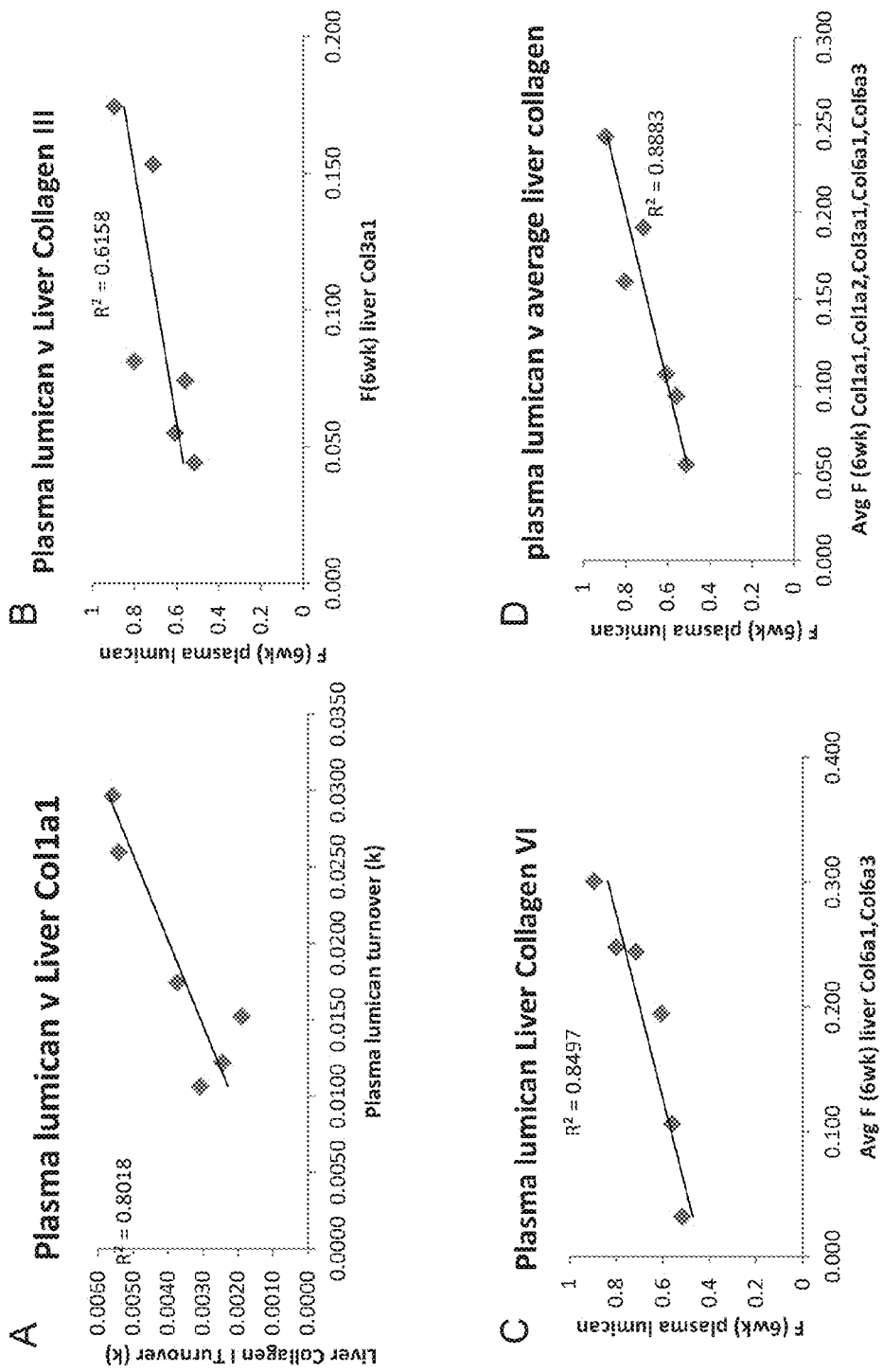
FIG. 5 shows the correlation between plasma lumican and liver collagen turnover. Comparisons are provided between liver collagen and plasma lumican turnover (A), plasma lumican and liver Collagen III α1 (B), plasma lumican and liver Collagen VI α3 (C), and plasma lumican and an average liver turnover derived from Collagens I α1, I α2, III α1, VI α1, and VI α3 (D).

Alterations in mass isotopomer pattern in peptides derived from many proteins in plasma, including peptides derived from the protein lumican, were identified and measured by LC/MS/MS and compared to synthesis rates of liver tissue collagens. Collagen synthesis rates in liver varied among individual human subjects (FIG. 3). The synthesis rate of plasma lumican was verified to closely reflect the synthesis rate of collagen Types I, III, and VI in the liver of the same patients with hepatitis and suspected fibrosis, indicating measurement of liver fibrogenesis rate from a blood measurement (FIGS. 4-5).

Figure 6:
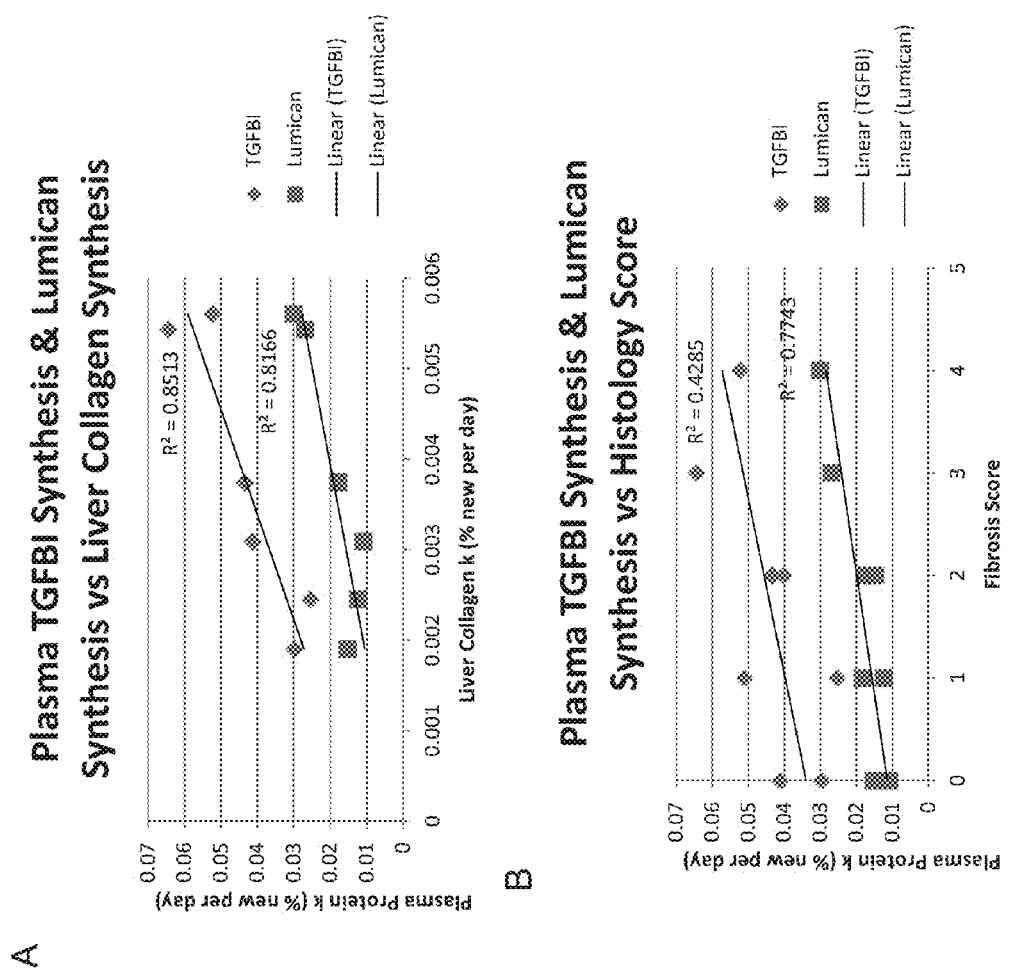
FIG. 6 shows that the rates of plasma lumican synthesis and plasma TGFBI synthesis correlate with each other and with liver collagen synthesis (A) and liver fibrosis score (B) in the same patients.
Figure 7:
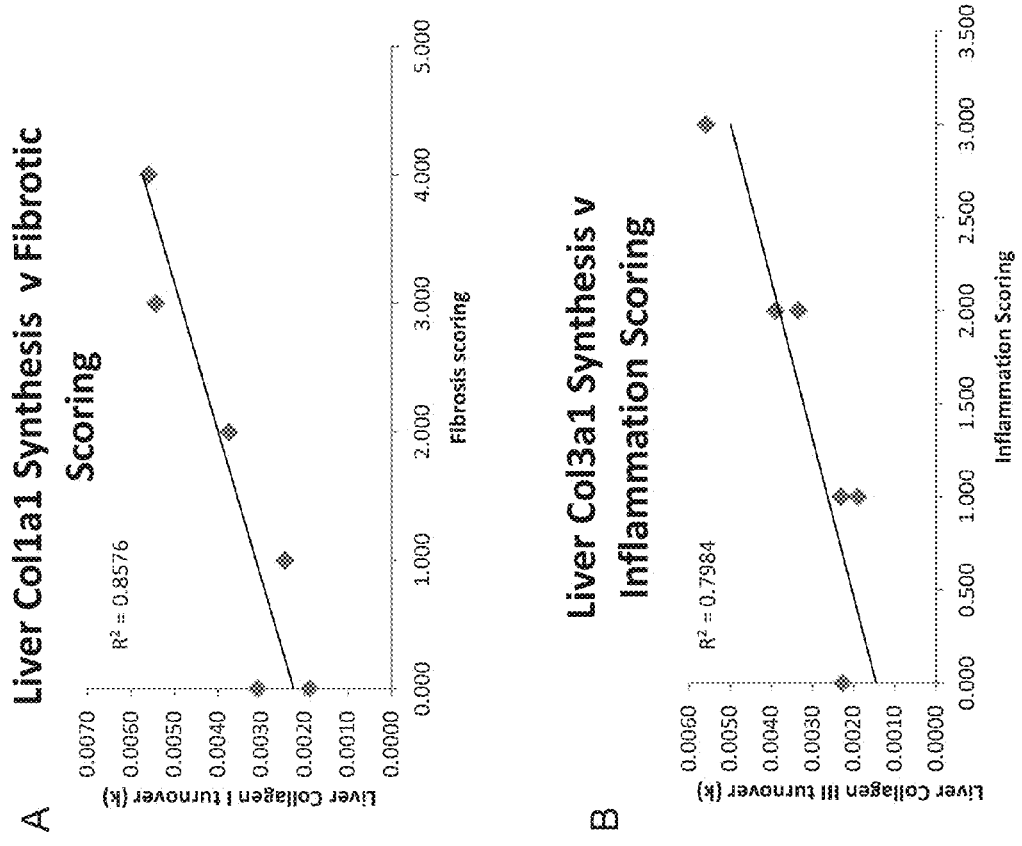
FIG. 7 shows the correlations between liver Collagen I α1 synthesis rate and liver fibrosis score (A) and between liver Collagen III α1 synthesis rate and liver inflammation score (B) in the same patients.
Figure 8:
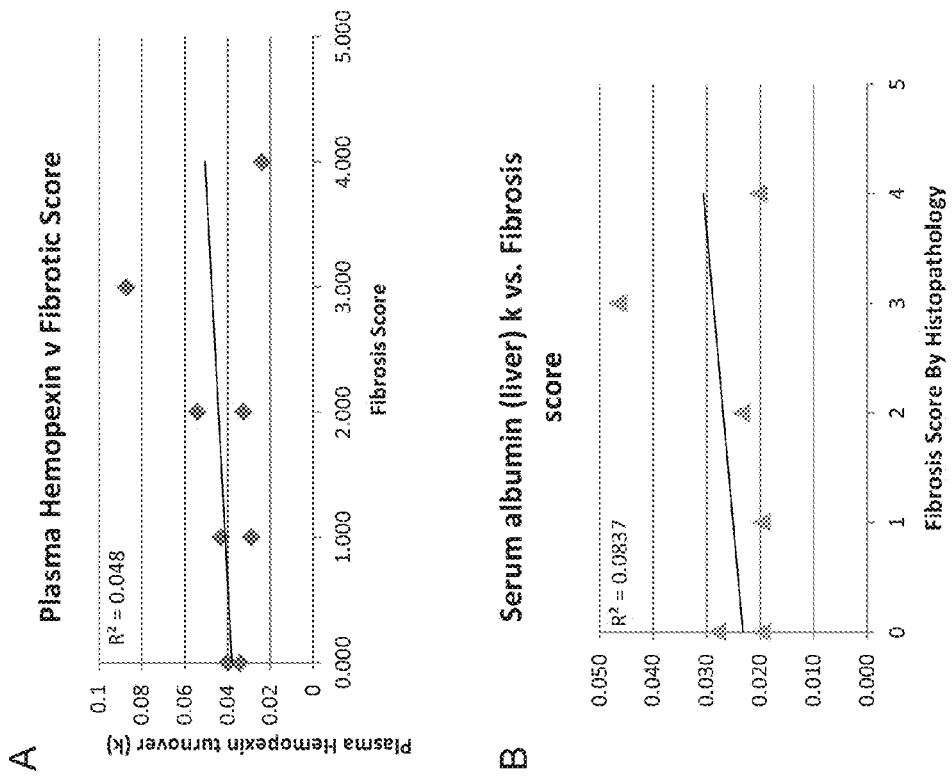
FIG. 8 shows that the synthesis rates of other selected proteins (plasma hemopexin, A and serum albumin, B) do not correlate with liver fibrosis score in the same patients.

Accordingly, the synthesis rate of lumican in blood plasma could be calculated from alterations in mass isotopomer pattern as represented by these data. Moreover, the synthesis rate of plasma transforming growth factor (TGF)-beta inducible protein was also shown to closely correlate with the synthesis rate of collagen type I α1 in the liver of patients with hepatitis (FIG. 6A) and suspected fibrosis in the same subjects (FIG. 6B). As illustrated in FIG. 7A, the synthesis rate of collagen type I in the liver of patients with hepatitis, and suspected fibrosis correlated with histologic fibrosis score in the same subjects. As illustrated in FIG. 7B, the synthesis rate of collagen type III in the liver of patients with hepatitis, and suspected fibrosis correlated with histologic inflammation score in the same subjects. In addition, the synthesis rates of most proteins in blood did not correlate with liver fibrosis scores (selected proteins as shown in FIG. 8), demonstrating that plasma protein synthesis rates are not a non-specific marker of an increase in general liver protein synthesis in these patients with hepatitis and suspected fibrosis.

Example 2

Virtual Biopsy of Creatine Kinase Using Blood Samples

Deuterated Water Labeling Protocol in Humans

All procedures and protocols were approved by the Institutional Review Board at Colorado State University. 17 subjects (7 males, 10 females) were included in the study, each volunteer was informed of the potential risks and benefits and provided written consent before participating. The study followed the guidelines set forth by the Declaration of Helsinki. Deuterium labeling of newly synthesized proteins was achieved by oral consumption of $^2H_2O$ (70%; Cambridge Isotope Laboratories, Andover Mass., USA) for 4 weeks using protocols described previously (Robinson et al, 2011). A target of 1-2% enrichment was achieved during a 1-week priming stage, when subjects consumed 50 ml of 70% $^2H_2O$ 3 times a day for a total of 150 ml/day, which was maintained for 3 weeks with a dose of 50 ml of 70% $^2H_2O$ 2 times a day for a total of 100 ml/day.

Sample Collection

Saliva swabs were collected periodically during oral deuterated water consumption, Participants were instructed to not eat or drink anything for 30 min before saliva sampling. Saliva swabs were stored at −80° C. until analysis. Venous blood was collected and plasma separated by centrifugation (1200 g, 4° C., 15 min) and stored at −80° C. Muscle biopsy samples (~100-150 mg) of the vastus lateralis were removed while the subjects were under local anesthesia (1% lidocaine) using a 5-mm Bergstrom needle with manual suction and then immediately frozen in liquid nitrogen and stored at −80° C.

Body Water Enrichment Analysis

Body water enrichment was determined from saliva swabs or plasma samples. Aliquots of plasma or saliva were diluted 1:200, and placed into the caps of inverted sealed screw-capped vials for overnight distillation at 80° C. Body water $2H_2O$ enrichments were determined by direct measurement of deuterium mole percent excess (MPE) in water distilled from the blood plasma. MPE was measured against a $^2H_2O$ standard curve using laser water isotope analyzer (LGR, Los Gatos Calif.).

SDS-PAGE Fractionation, Coomassie Staining and In-Gel Trypsin Digestion of Muscle Proteins 10-30 mg muscle samples were homogenized in M-PER reagent (Thermo) at 100 mg/ml with 1× protease inhibitor cocktail (Thermo). The homogenate was centrifuged at 1000×g for 10 min at 4° C. to pellet insoluble material. 250 µg of protein from homogenate was prepared for SDS-PAGE and LC/MS. The samples were incubated at 95° C. for 5 min in 1×XT sample buffer (Bio-Rad) and 5 mM TCEP (Sigma). The samples were allowed to cool to room temperature and Iodoacetamide (Sigma) was added at a final concentration of 15 mM. The samples were incubated at room temperature in the dark for 20 min. The samples were loaded onto Criterion XT 12 well 4-12% Bis-Tris gels (Bio-Rad) with 1×XT MES running buffer (Bio-Rad) in the Bio-Rad Criterion Cell (165-6001). 10 µL of Kaliedoscope Pre-Stained Molecular Weight Standard (Bio-Rad) was loaded on flanking ends of the samples. The gels were run at 60V for 20 minutes to allow the samples to fully enter the gel and then run at 100V for 1 and a half hours. The gels were removed and washed 3 times with 200 ml of MilliQ H2O for 5 minutes with rotation. Coomassie (Bio-Rad) was added to barely cover the gels and incubated for 60 minutes with rotation. The gels were destained by washing 4 times with 200 ml of MilliQ H2O for 30 minutes with rotation; a Kimwipe was placed in the water to help absorb the stain. The gel-bands corresponding to 10-15, 15-20, 20-25, 25-37, 37-50, 50-75, 75-100, 100-150 and 150-250 kD were excised from the Coomassie-stained gels and subjected to overnight trypsin (Proteomics grade, Sigma) digestion at 37 C. The peptides were extracted from the gel, dried, reconstituted in 3% acetonitrile/0.1% formic acid for LC/MS analysis.

Immunoprecipitation of Creatine Kinase M-Type from Plasma, SDS-PAGE Fractionation and In-Gel Trypsin Digestion Creatine-kinase M-type (CK-M) was immunoprecipitated from ~500 µl plasma using 20 µg of goat-anti-CK-M polyclonal antibody (CalBioreagents) conjugated to 1 mg epoxy Dynabeads (Invitrogen). Samples were incubated for 60 min at RT and the bound CK-M was eluted in sample buffer and prepared for SDS-PAGE fractionation and Coomassie staining as described above. The gel-band corresponding to 37-50 kD were excised from the Coomassie-stained gels and subjected to overnight trypsin (Proteomics grade, Sigma) digestion at 37° C. The peptides were extracted from the gel, dried, reconstituted in 3% acetonitrile/0.1% formic acid for LC/MS analysis.

LC/MS Analysis

The trypsin-digested peptides were analyzed on an Agilent 6520 or 6550 QToF with Chip Nano source and 1200 series nanoflow and capillary HPLC pumps (Agilent Technologies, Santa Clara, Calif.) as described previously (Price et al. 2011, 2012). Each sample was injected twice per analysis using a Polaris HR chip (Agilent #G4240-62030) consisting of a 360 nL enrichment column and a 0.075×150 mm analytical column, both packed with Polaris C18-A stationary phase (3 µm particle size). Mobile phase for the nano LC was 3% v/v acetonitrile, 0.1% formic acid, in 18MΩ water (Buffer A) and 95% acetonitrile, 0.1% formic acid in 18 MΩ water (Buffer B). Samples were eluted at a flow rate of 350 nL/min with an 18-27-min gradient. During the first injection, data dependent MSMS fragmentation spectra were collected with the instrument set to collect 6 MS scans per second, 4 MSMS spectra per second, and up to 12 precursors per cycle. During the second injection, no MSMS fragmentations were performed and a longer dwell time (1 spectrum per second) was used in the full scan acquisition. The longer dwell time increased the signal to noise ratio for the observed isotopomer patterns. MSMS fragmentation data were analyzed using Spectrum Mill MS Proteomics Workbench (version B.04.00, Agilent Technologies, Santa Clara, Calif.) using the Swiss-Prot mouse database (August 2010) with a global false discovery rate of 1%. Fixed modifications (carbamidomethylation of cysteine) and variable modifications (oxidized methionine, pyroglutamic acid) were enabled and up to two missed cleavages allowed. Results validated at the peptide and protein level were searched again allowing for non-specific cleavage of the protein. A list of peptides with scores greater than 6 and scored peak intensities greater than 50% was exported from Spectrum Mill and collapsed into a non-redundant peptide formula database using Excel. This database, containing peptide elemental composition, mass, and retention time, was used to extract peptide isotopomer abundances (containing kinetic information) of each peptide from corresponding MS-only acquisition files with the Find-by-Formula algorithm in Mass Hunter (version B.05.00, Agilent Technologies, Santa Clara, Calif.). A visual basic application was constructed to calculate peptide elemental composition from lists of peptide sequences and calculate isotopomer patterns over a range of precursor body 2H2O enrichments (p) for the number (n) of C—H positions actively incorporating hydrogen/deuterium (H/D) from body water. Subsequent data handling was performed using a series of Microsoft Excel templates, with input of body water enrichment for each subject to yield fractional synthesis data at the protein level. The kinetics data were filtered to include ≥2 peptides per protein.

Statistical Analysis

Pearson correlation analysis (GraphPad Prism) was performed to correlate the fractional synthesis of CK-M in the plasma to that measured in the muscle. In addition, correlation analysis was also performed with fractional synthesis of plasma CK-M and that of several myofibril and cytosolic proteins measured in the muscle. All correlations were considered significant at p<0.05.

Figure 9:
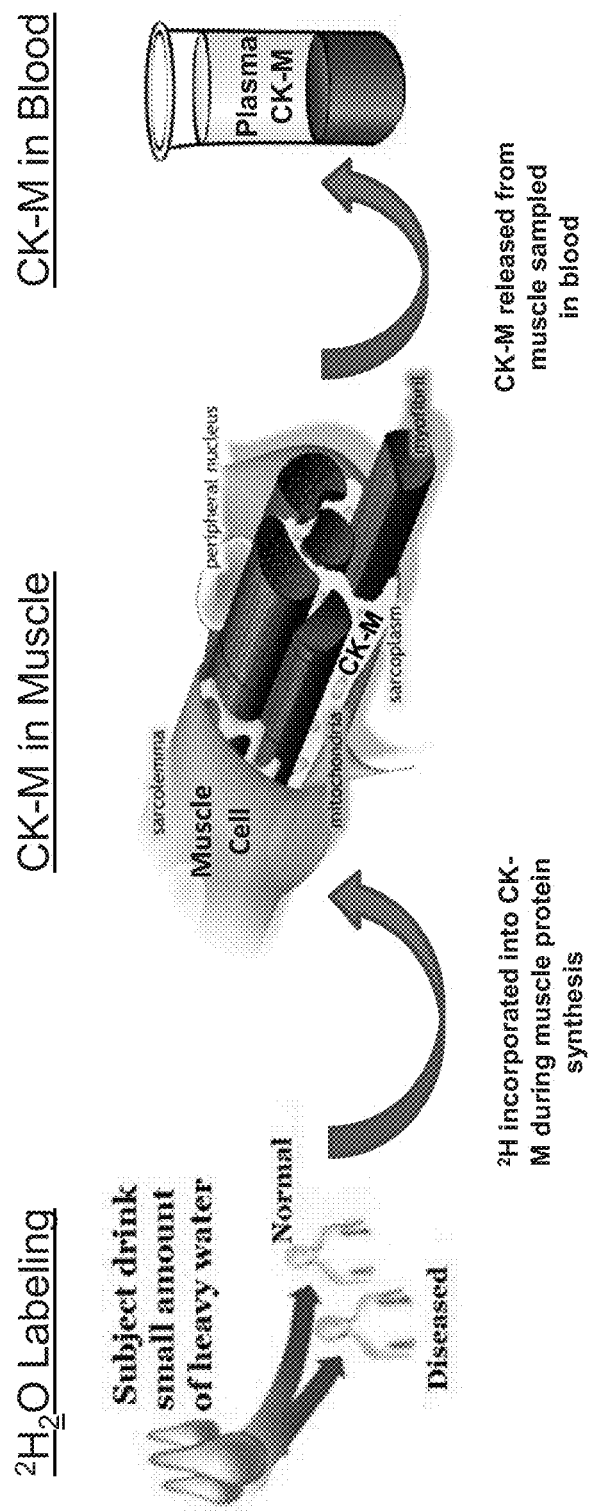
FIG. 9 illustrates an application of the "virtual biopsy" method to assess muscle protein synthesis from measurements of isotope-labeled muscle creatine kinase in the blood.
Figure 10:
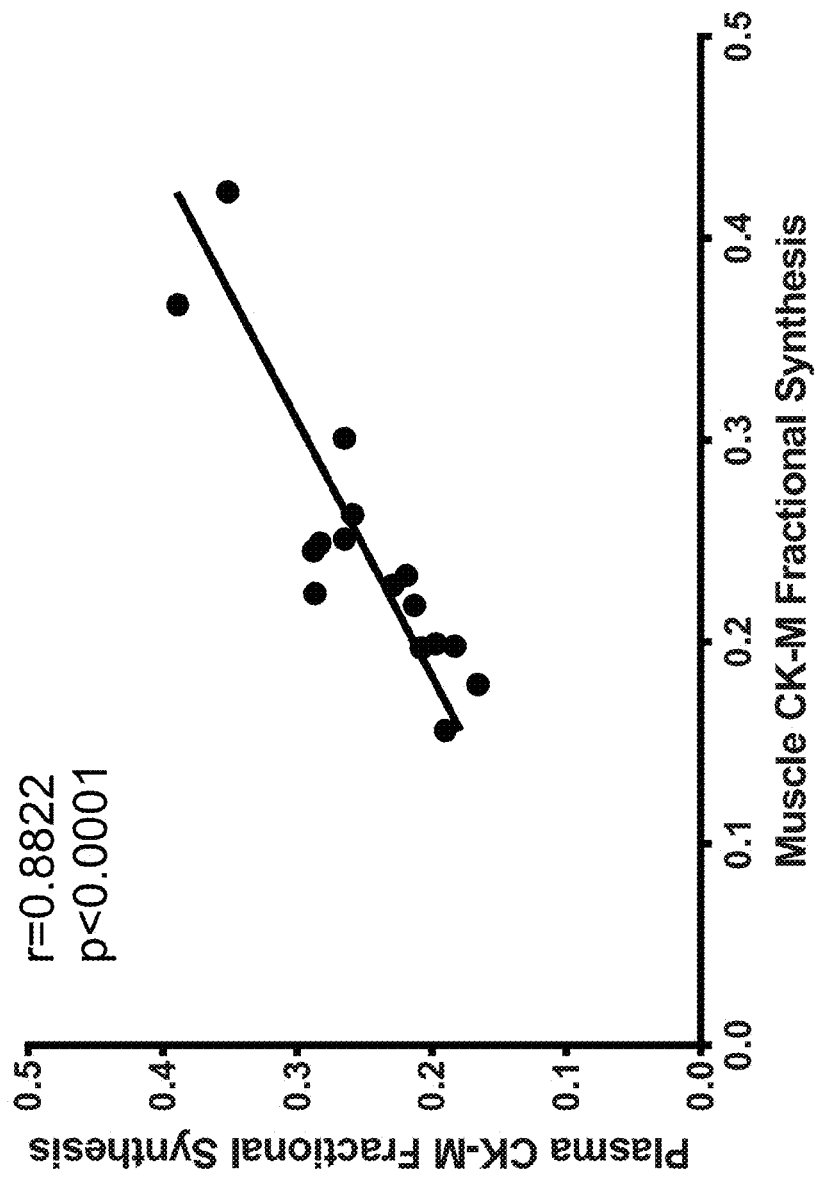
FIG. 10 shows the correlation between rates of plasma creatine kinase MM synthesis and muscle creatine kinase MM synthesis. r- and p-values are also provided.
Figure 11:
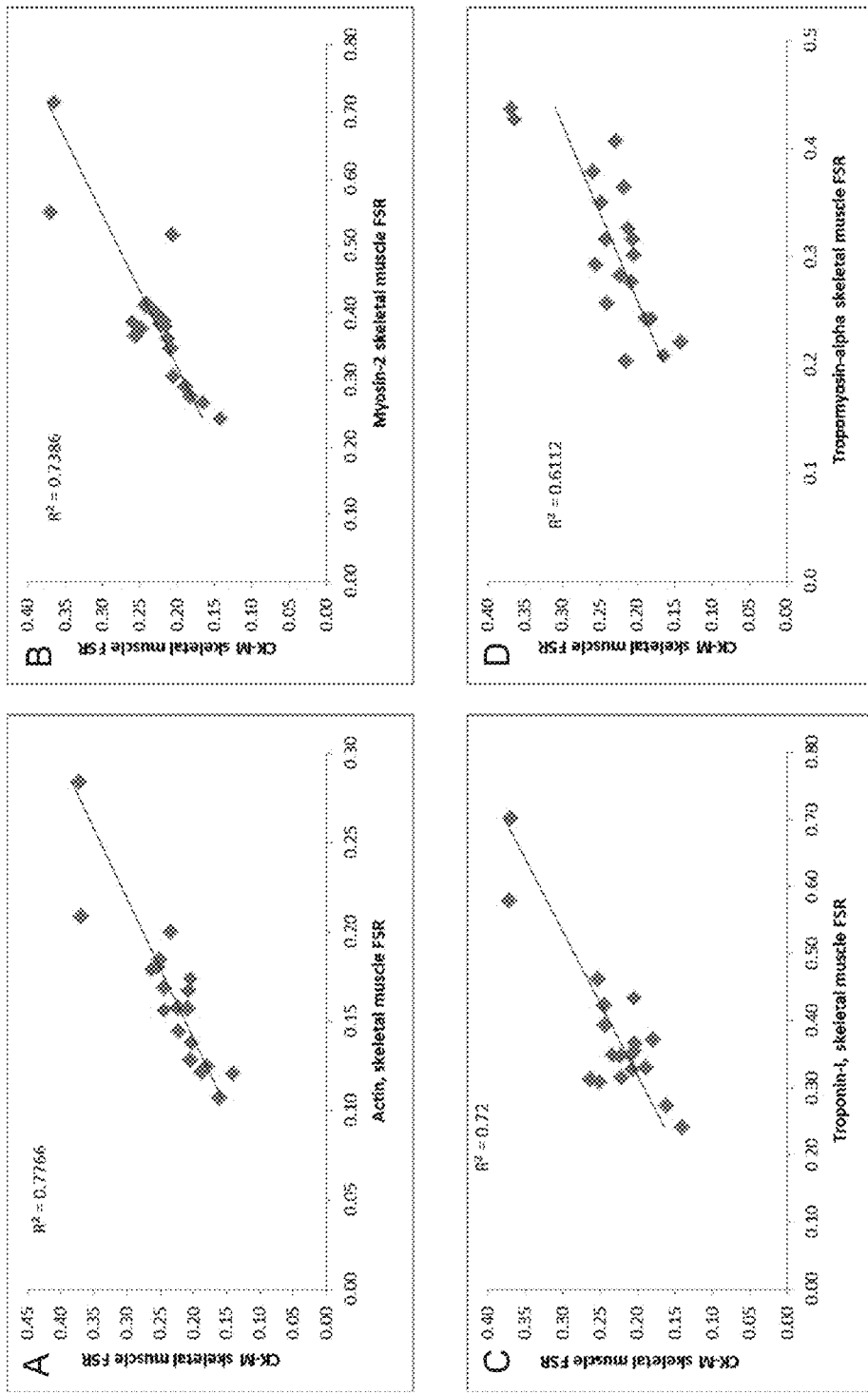
FIG. 11 shows that the synthesis rates of several muscle proteins correlate with the synthesis rate of muscle creatine kinase MM. Shown are the correlations between muscle creatine kinase MM synthesis rate and the synthesis rates of Actin (A), Myosin-2 (B), Troponin-I (C), and Tropomyosin-alpha (D).

Results $^2H_2O$ was administered to humans or experimental animals, and plasma creatine kinase MM was isolated from plasma by immunoprecipitation, subjected to trypsin digestion, and analyzed by LC/MS/MS (liquid chromatography-tandem mass spectrometry) to determine alterations in mass isotopomer pattern, from which the synthesis rate of creatine kinase MM in blood plasma was calculated (FIG. 9). The synthesis rate of plasma creatine kinase MM was verified to closely reflect the synthesis rate of creatine kinase MM isolated from muscle biopsies in the same subjects (FIG. 10). As illustrated in FIG. 11, the synthesis rates of skeletal muscle creatine kinase MM closely correlated with the synthesis rates of several other muscle proteins (Actin, FIG. 11A; Myosin-2, FIG. 11B; Troponin-I, FIG. 11C; Tropomyosin-alpha, FIG. 11D). In contrast, creatine kinase MB (cardiac muscle-specific) that was isolated from plasma exhibited much higher synthesis rates than creatine kinase MM, indicating tissue-specific measurement of creatine kinase synthesis from blood measurements.

Figure 12:
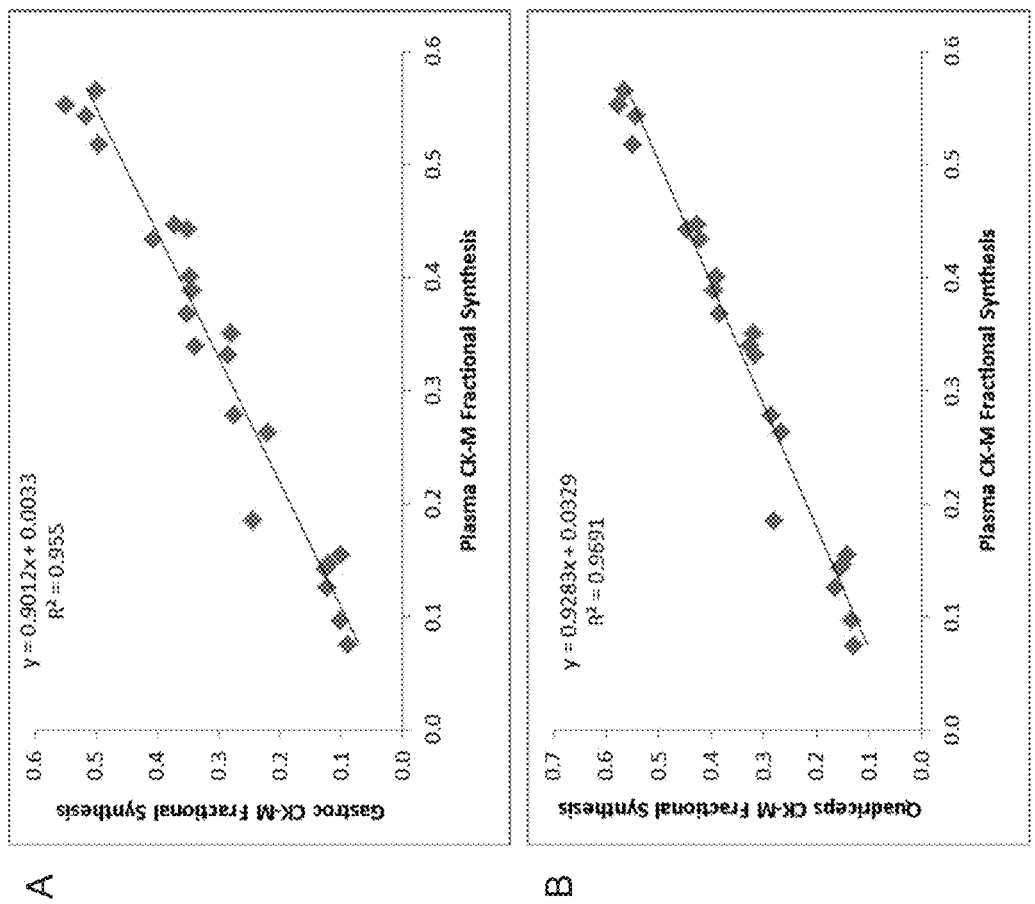
FIG. 12 shows that the synthesis rate of plasma creatine kinase MM correlates with creatine kinase MM isolated from different muscle types. Shown are the correlations between plasma creatine kinase MM synthesis rate and the synthesis rates of creatine kinase MM isolated from the gastrocnemius (A) and quadriceps (B) muscles.

In a parallel experiment in rats, $^2H_2O$ was administered to healthy rats, and plasma creatine kinase MM was isolated from plasma by immunoprecipitation, subjected to trypsin digestion, and analyzed by LC/MS/MS (liquid chromatography-tandem mass spectrometry) to determine alterations in mass isotopomer pattern, from which the synthesis rate of creatine kinase MM in blood plasma was calculated (as depicted in FIG. 9). The synthesis rates of plasma creatine kinase MM correlated extremely closely with the synthesis rate of gastrocnemius muscle creatine kinase MM (FIG. 12A) and the synthesis rate of quadriceps muscle creatine kinase MM (FIG. 12B).

REFERENCES

1. G. L is, L. I. Wassenaar, M. J. Hendry, High-precision laser spectroscopy D/H and $^{18}O/^{16}O$ measurements of microliter natural water samples, Anal. Chem. 80 (2008) 287-293.

2. M. K. Hellerstein, R. A. Neese, Mass isotopomer distribution analysis at eight years: theoretical, analytic, and experimental considerations, Am. J. Physiol. 276 (1999) E1146-E1170.

3. J. C. Price, W. E. Holmes, K. W. Li, N. A. Floreani, R. A. Neese, S. M. Turner, M. K. Hellerstein, Measurement of human plasma proteome dynamics with $^2H_2O$ and liquid chromatography tandem mass spectrometry, Anal. Biochem. 420 (2012) 73-83.

What is claimed is:

1. A method for measuring the rate of synthesis, breakdown, transport, or other kinetic parameters of a protein in a tissue of medical interest, without requiring physical sampling of said tissue, by a measurement of the protein in a body fluid, the method comprising:
   a) selecting one or more target proteins in a tissue;
   b) administering an isotope-labeled molecule to a subject for a period of time sufficient for said isotope-labeled molecule to enter into and label the one or more target proteins to produce one or more isotope-labeled target proteins;
   c) collecting a volume of a body fluid, wherein said volume comprises one or more isotope-labeled target proteins that escaped or were released from the tissue;
   d) enriching or isolating the one or more isotope-labeled target proteins from said volume;
   e) performing a mass spectrometric measurement of the isotopic content, rate of incorporation, and/or pattern or rate of change in isotopic content and/or pattern of isotope labeling of the one or more enriched or isolated isotope-labeled target proteins;
   f) calculating at least one kinetic parameter of the one or more enriched or isolated isotope-labeled target proteins, wherein the kinetic parameter of the one or more isotope-labeled target proteins from said volume of a body fluid reflects the corresponding kinetic parameter of the one or more target proteins in said tissue; and
   g) inferring the at least one kinetic parameter of the one or more target proteins in the tissue based on the corresponding at least one kinetic parameter of the one or more target proteins in the body fluid.

2. The method of claim 1, wherein the isotope-labeled molecule is a general precursor that labels amino acids.

3. The method of claim 2, wherein the isotope-labeled molecule is selected from the group consisting of $^2H_2O$, $^{13}C_2$-leucine, $^3H$-phenylalanine, $^{15}N$-glycine, $^{15}N$-labeled spirulina, $^{13}CO_2$, $^2H_3$-leucine, and $^{13}C$-glucose.

4. The method of claim 1, wherein the isotope-labeled molecule is a stable, non-radioactive isotope-labeled molecule.

5. The method of claim 4, wherein the isotope-labeled molecule is $^2H_2O$.

6. The method of claim 1, wherein the isotope-labeled molecule is a radioactive isotope-labeled molecule.

7. The method of claim 1, wherein the tissue is selected from the group consisting of skeletal muscle, heart muscle, brain, pancreatic β-cells or islets, and collagen-producing fibroblasts present in liver, lung, kidney, heart, or skin.

8. The method of claim 1, wherein the body fluid is selected from the group consisting of blood, urine, sputum, bile, cerebrospinal fluid, interstitial fluid of skin or adipose tissue, saliva, tears, bronchial-alveolar lavage, oropharyngeal secretions, intestinal fluids, cervico-vaginal or uterine secretions, and seminal fluid.

9. The method of claim 1, wherein the kinetic parameter of the one or more isotope-labeled target proteins from said volume of a body fluid has been established to reflect the corresponding kinetic parameter of the one or more target proteins in said tissue by independently comparing measurements of the kinetic parameter of the one or more target proteins in individual subjects.

10. The method of claim 1, wherein the isotope-labeled molecule is administered for a period of time sufficient to produce one or more isotope-labeled target proteins and then discontinued, and wherein enriching or isolating the one or more isotope-labeled target proteins from the volume of a body fluid takes place after the administration of the isotope-labeled molecule has been discontinued.

11. The method of claim 1, wherein the one or more target proteins are related to tissue collagen deposition or fibril formation and/or are derived from collagen-synthesizing fibroblasts.

12. The method of claim 1, wherein the one or more target proteins are selected from the group consisting of lumican, perlecan, fibronectin, procollagen, and collagen.

13. The method of claim 11, wherein the at least one kinetic parameter reveals a rate of a medically important process for the diagnosis, therapy, prognosis, management, stratification, or other characterization of a disease selected from the group consisting of hepatitis C or B; alcoholic liver fibrosis; fatty liver disease; fibrosis of liver, lung, heart, skin, or kidney; and other fibrogenic disorders.

14. The method of claim 12, wherein the at least one kinetic parameter reveals a rate of a medically important process for the diagnosis, therapy, prognosis, management, stratification, or other characterization of a disease selected from the group consisting of hepatitis C or B; alcoholic liver fibrosis; fatty liver disease; fibrosis of liver, lung, heart, skin, or kidney; and other fibrogenic disorders.

15. The method of claim 12, wherein the one or more target proteins are subjected to trypsin digestion between steps (d) and (e), and the one or more target proteins are analyzed as trypsin-digested peptides in step (e).

16. The method of claim 1, wherein the target protein is creatine kinase MM or creatine kinase MB.

17. The method of claim 16, wherein the body fluid is plasma; step (d) comprises immunoprecipitation; said creatine kinase MM or creatine kinase MB is subjected to trypsin digestion between steps (d) and (e); and said creatine kinase MM or creatine kinase MB is analyzed as a trypsin-digested peptide in step (e).

18. The method of claim 17, wherein step (e) comprises measuring mass isotopomer abundance by LC/MS/MS.

19. The method of claim 18, wherein creatine kinase MM-specific trypsin-digested peptides are analyzed by LC/MS/MS for alterations in mass isotopomer abundance, and wherein said alterations in mass isotopomer abundance are used to calculate a rate of synthesis and/or breakdown of creatine kinase in skeletal muscle tissue.

20. The method of claim 19, wherein the calculation of the rate of synthesis and/or breakdown of creatine kinase in skeletal muscle tissue is used in the diagnosis, management, rehabilitation, or treatment selection of a patient with sarcopenia, cachexia, malnutrition, frailty, mobility disability, muscular dystrophy, or another disorder of skeletal muscle mass or function.

21. The method of claim 18, wherein creatine kinase MB-specific trypsin-digested peptides are analyzed by LC/MS/MS for alterations in mass isotopomer abundance, and wherein said alterations in mass isotopomer abundance are used to calculate a rate of synthesis and/or breakdown of creatine kinase in cardiac tissue.

22. The method of claim 21, wherein the calculation of the rate of synthesis and/or breakdown of creatine kinase in cardiac tissue is used in the diagnosis, management, rehabilitation, or treatment selection of a patient with heart failure, heart transplant, hypertension ischemic heart disease, or another disorder of cardiac mass or function.

23. The method of claim 1, wherein the one or more target proteins are blood proteins derived from pancreatic β-cell secretory granules.

24. The method of claim 1, wherein the at least one kinetic parameter reveals a rate of a medically important process for the diagnosis, therapy, prognosis, management, stratification, or other characterization of a disease process in a tissue of medical interest.

25. The method of claim 1, wherein the calculation of the at least one kinetic parameter of the one or more target proteins is used as a diagnostic test.

26. The method of claim 25, wherein the diagnostic test is used in the diagnosis, management, or treatment selection of a human or veterinary patient.

* * * * *